US008765139B2

(12) United States Patent
Palese et al.

(10) Patent No.: US 8,765,139 B2
(45) Date of Patent: *Jul. 1, 2014

(54) ATTENUATED NEGATIVE STRAND VIRUSES WITH ALTERED INTERFERON ANTAGONIST ACTIVITY FOR USE AS VACCINES AND PHARMACEUTICALS

(75) Inventors: Peter Palese, Leonia, NJ (US); Adolfo Garcia-Sastre, New York, NY (US); Thomas Muster, Vienna (AT)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/250,846

(22) Filed: Sep. 30, 2011

(65) Prior Publication Data
US 2012/0258134 A1 Oct. 11, 2012

Related U.S. Application Data

(60) Division of application No. 12/148,798, filed on Apr. 22, 2008, now Pat. No. 8,057,803, which is a continuation of application No. 10/713,732, filed on Nov. 14, 2003, now Pat. No. 7,588,768, which is a continuation of application No. 09/332,288, filed on Jun. 11, 1999, now Pat. No. 6,669,943.

(60) Provisional application No. 60/117,683, filed on Jan. 29, 1999, provisional application No. 60/108,832, filed on Nov. 18, 1998, provisional application No. 60/089,103, filed on Jun. 12, 1998.

(51) Int. Cl.
*A61K 39/145* (2006.01)
*A61K 39/12* (2006.01)
*A01N 63/00* (2006.01)
*A61K 39/38* (2006.01)
*A61K 39/25* (2006.01)

(52) U.S. Cl.
USPC ............. 424/206.1; 424/209.1; 424/199.1; 424/184.1; 424/93.6

(58) Field of Classification Search
None
See application file for complete search history.

(56) References Cited

U.S. PATENT DOCUMENTS

| | | | |
|---|---|---|---|
| 4,071,618 A | 1/1978 | Konobe et al. | |
| 4,567,147 A | 1/1986 | Ooi et al. | |
| 4,659,569 A | 4/1987 | Mitsuhashi et al. | |
| 5,166,057 A | 11/1992 | Palese et al. | |
| 5,674,502 A | 10/1997 | Ennis et al. | |
| 5,766,601 A | 6/1998 | Ennis | |
| 5,786,199 A | 7/1998 | Palese et al. | |
| 5,820,871 A | 10/1998 | Palese et al. | |
| 5,854,037 A | 12/1998 | Palese et al. | |
| 5,866,694 A | 2/1999 | Katinger et al. | |
| 5,882,650 A | 3/1999 | Ennis | |
| 6,146,642 A | 11/2000 | Garcia-Sastre et al. | |
| 6,146,873 A | 11/2000 | Kistner et al. | |
| 6,300,090 B1 | 10/2001 | Steinman et al. | |
| 6,326,151 B1 | 12/2001 | Katze et al. | |
| 6,468,544 B1 | 10/2002 | Egorov et al. | |
| 6,544,785 B1 | 4/2003 | Palese et al. | |
| 6,573,079 B1 | 6/2003 | Palese et al. | |
| 6,635,416 B2 | 10/2003 | Palese et al. | |
| 6,669,943 B1 | 12/2003 | Palese et al. | |
| 6,673,591 B2 | 1/2004 | Lau | |
| 6,686,190 B2 | 2/2004 | Lau | |
| 6,800,288 B2 | 10/2004 | Ferko et al. | |
| 6,852,522 B1 | 2/2005 | Palese et al. | |
| 6,866,853 B2 | 3/2005 | Egorov et al. | |
| 6,884,414 B1 | 4/2005 | Palese et al. | |
| 7,060,430 B2 | 6/2006 | Palese et al. | |
| 7,132,271 B2 | 11/2006 | Lau | |
| 7,344,722 B1 | 3/2008 | Maassab et al. | |
| 7,442,527 B2 | 10/2008 | Palese et al. | |
| 7,494,659 B2 | 2/2009 | Katinger et al. | |
| 7,494,808 B2 | 2/2009 | Palese et al. | |
| 7,588,768 B2 | 9/2009 | Palese et al. | |
| 7,833,774 B2 | 11/2010 | Palese et al. | |
| 8,057,803 B2 | 11/2011 | Palese et al. | |
| 8,124,101 B2 | 2/2012 | Palese et al. | |
| 8,137,676 B2 | 3/2012 | Palese et al. | |
| 2004/0109877 A1 | 6/2004 | Palese et al. | |
| 2004/0253273 A1 | 12/2004 | Paleso et al. | |
| 2005/0054074 A1 | 3/2005 | Palese et al. | |
| 2006/0216701 A1 | 9/2006 | Palese et al. | |

(Continued)

FOREIGN PATENT DOCUMENTS

DE 100 20 505 10/2001
EP 0 702 085 A1 3/1996

(Continued)

OTHER PUBLICATIONS

Aebi, 1989, "cDNA structures and regulation of two interferon-induced human Mx proteins." in Mol. Cell. Biol.; 9(11):5062-72.
Baskin et al., 2007, "Functional genomic and serological analysis of the protective immune response resulting from vaccination of macaques with an NS1-truncated influenza virus," J Virol. Nov; 81(21):11817-27.
Basler et al., The Ebola virus VP35 protein functions as a type I IFN antagonist. Proc Nat Acad Sci U S A. Oct. 24, 2000;97(22):12289-94.

(Continued)

*Primary Examiner* — Benjamin P Blumel
(74) *Attorney, Agent, or Firm* — Jones Day

(57) ABSTRACT

The present invention relates, in general, to attenuated negative-strand RNA viruses having an impaired ability to antagonize the cellular interferon (IFN) response, and the use of such attenuated viruses in vaccine and pharmaceutical formulations. The invention also relates to the development and use of IFN-deficient systems for selection of such attenuated viruses.
In particular, the invention relates to attenuated influenza viruses having modifications to the NS1 gene that diminish or eliminate the ability of the NS1 gene product to antagonize the cellular IFN response. The mutant viruses replicate in vivo but demonstrate reduced pathogenicity, and therefore are well suited for live virus vaccines, and pharmaceutical formulations.

28 Claims, 3 Drawing Sheets

(56) References Cited

U.S. PATENT DOCUMENTS

Figure 1:
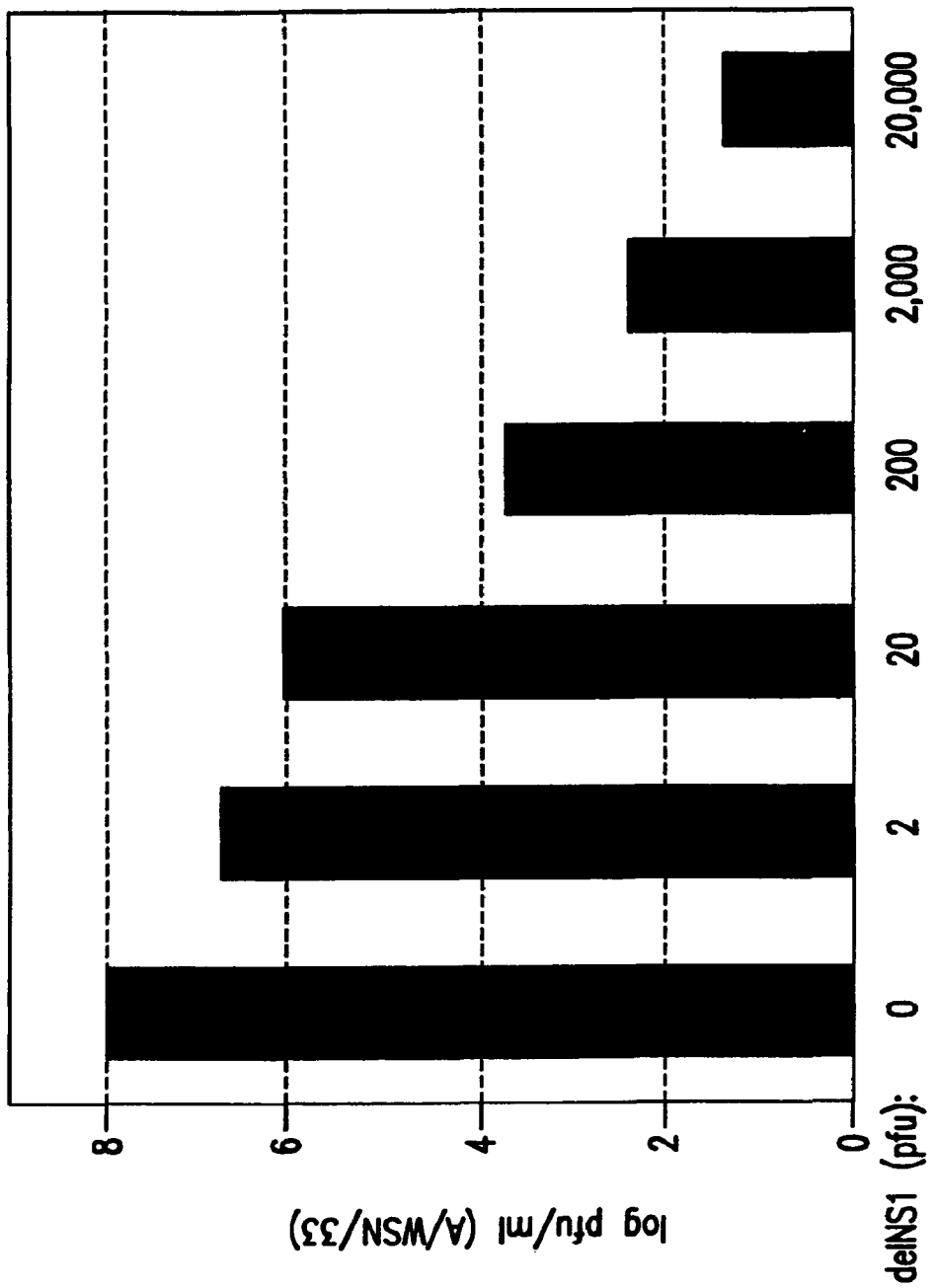

| | | | |
|---|---|---|---|
| 2007/0122430 | A1 | 5/2007 | Shneider et al. |
| 2007/0172929 | A1 | 7/2007 | Maassab et al. |
| 2008/0050402 | A1 | 2/2008 | Zhou et al. |
| 2008/0234175 | A1 | 9/2008 | Montelione et al. |
| 2008/0254060 | A1 | 10/2008 | Palese et al. |
| 2009/0010962 | A1 | 1/2009 | Palese et al. |
| 2009/0028901 | A1 | 1/2009 | Palese et al. |
| 2009/0123495 | A1 | 5/2009 | Sachet et al. |
| 2009/0203114 | A1 | 8/2009 | Palese et al. |
| 2010/0080827 | A1 | 4/2010 | Palese et al. |
| 2010/0158942 | A1 | 6/2010 | Palese et al. |
| 2010/0233785 | A1 | 9/2010 | Brandt et al. |
| 2013/0034581 | A1 | 2/2013 | Palese et al. |

FOREIGN PATENT DOCUMENTS

| | | | |
|---|---|---|---|
| EP | 0 780 475 | A1 | 6/1997 |
| EP | 0 780 475 | B1 | 6/1997 |
| EP | 1 085 904 | A1 | 12/1999 |
| EP | 1 086 207 | | 1/2007 |
| EP | 1 773 384 | | 4/2007 |
| EP | 1 855 713 | | 11/2007 |
| EP | 1 098 961 | B1 | 1/2008 |
| EP | 1 962 893 | | 9/2008 |
| EP | 2 316 923 | | 5/2011 |
| EP | 2 316 924 | | 5/2011 |
| EP | 2 497 492 | | 9/2012 |
| JP | 59-39831 | | 3/1984 |
| WO | WO 96/10632 | | 4/1996 |
| WO | WO 96/34625 | A1 | 11/1996 |
| WO | WO 97/06270 | A1 | 2/1997 |
| WO | WO 97/08292 | | 3/1997 |
| WO | WO 97/12032 | A1 | 4/1997 |
| WO | WO 98/02530 | A1 | 1/1998 |
| WO | WO 98/13501 | A2 | 4/1998 |
| WO | WO 98/53078 | A1 | 11/1998 |
| WO | WO 99/02657 | A1 | 1/1999 |
| WO | WO 99/15672 | A1 | 4/1999 |
| WO | WO 99/64068 | A1 | 12/1999 |
| WO | WO 99/64570 | A | 12/1999 |
| WO | WO 99/64571 | A1 | 12/1999 |
| WO | WO 01/64860 | | 9/2001 |
| WO | WO 01/77394 | | 10/2001 |
| WO | WO 02/24876 | | 3/2002 |
| WO | WO 2006/083286 | | 8/2006 |
| WO | WO 2006/088481 | | 8/2006 |
| WO | WO 2007/064802 | | 6/2007 |

OTHER PUBLICATIONS

Beattie et al., 1995, "Reversal of the Interferon-Sensitive Phenotype of a Vaccinia Virus Lacking EL3 by Expression of the Reovirus S4 Gene", J. Virol. 69(1):499-505.
Bergmann et al., 2000, "Influenza virus NS1 protein counteracts PKR-mediated inhibition of replication," J Virol. Jul;74(13):6203-6.
Bossert et al., 2002, "Respiratory Syncytial Virus (RSV) Nonstructural (NS) Proteins as Host Range Determinants: a Chimeric Bovine RSV with NS Genes from Human RSV Is Attenuated in Interferon-Competent Bovine Cells", J. of Virology 76:4287-93.
Bouloy et al., 2001, "Genetic evidence for an interferon-antagonistic function of rift valley fever virus nonstructural protein NSs.", J. Virol. 75(3):1371-7.
Briedis et al., 1981, "Influenza B virus genome: sequences and structural organization of RNA segment 8 and the mRNAs coding for the $NS_1$ and $NS_2$ proteins." J Virol. 42(1):186-93.
Buonagurio et al., 1984, "Analysis of an influenza A virus mutant with a deletion in the NS segment," J Virol. 49:418-425.
Chambers et al., 2009, "Influenza A viruses with truncated NS1 as modified live virus vaccines: Pilot studies of safety and efficacy in horses," Equine Veterinary Journal 41:87-92.
Clemens et al., 1997, "The Double Stranded RNA-Dependent Protein Kinase PKR: Structure and Function", in Journal of Interferon and Cytokine Research; 17:503-24.

Didcock et al., 1999, "The V Protein of Simian Virus 5 Inhibits Interferon Signaling by Targeting STAT1 for Proteasome-Mediated Degradation", J. Virol. 73(12):9928-33.
Donelan et al., 2004, "The N- and C-terminal domains of the NS1 protein of influenza B virus can independently inhibit IRF-3 and beta interferon promoter activation," J Virol. Nov; 78(21):11574-82.
Donelan et al., 2003, "recombinant influenza A virus expressing an RNA-binding-defective NS1 protein induces high levels of beta interferon and is attenuated in mice," J Virol. Dec; 77(24):13257-66.
Falcon et al., 2005, "Attenuation and immunogenicity in mice of temperature-sensitive influenza viruses expressing truncated NS1 proteins. J Gen Virol.," Oct; 86(Pt 10):2817-21.
Fernandez-Sesma et al., 2006, "Influenza virus evades innate and adaptive immunity via the NS1 protein," J Virol. Jul; 80(13):6295-304.
Floyd-Smith et al., 1981, "Interferon Action: RNA Cleavage Pattern of a (2'-5') Oligoadenylate-Dependent Endonuclease," Science; 212:1030-2.
Fodor et al., 1999, "Rescue of influenza A virus from recombinant DNA," J. Virol.; 73:9679-82.
Garcin et al., 1999, "Sendai Virus C Proteins Counteract the Interferon-Mediated Induction of an Antiviral State", J. Virol. 73(8): 6559-65.
Geiss et al., 2002, "Cellular transcriptional profiling in influenza A virus-infected lung epithelial cells: the role of the nonstructural NS1 protein in the evasion of the host innate defense and its potential contribution to pandemic influenza," Proc Natl Acad Sci U S A. Aug 6;99(16):10736-41.
Gonzalo et al., 1999, "Enhanced CD8+ T cell response to HIV-1 env by combined immunization with influenza and vaccinia virus recombinants." Vaccine 17(7-8):887-92.
Gorse et al., 1995, "Increased anti-influenza A virus cytotoxic T cell activity following vaccination of the chronically ill elderly with live attenuated or inactivated influenza virus vaccine." in J. Infect. Dis.; 172:1-10.
Gorse et al., 1990, "Enhancement of anti-influenza A virus cytotoxicity following influenza A virus vaccination in older, chronically ill adults." in J. Clin. Microbiol.; 28:2539-50.
Gotoh et al., 1999, "Knockout of the Sendai Virus C Gene Eliminates the Viral Ability to Prevent the Interferon-α/β-Mediated Responses." FEBS Lett. 459(2):205-10.
Hamzawi et al., 1981, "Antigenicity in hamsters of inactivated vaccines prepared from recombinant influenza viruses." J Hyg (Lond). 87(3):453-64 (Abstract previously submitted as reference C42 in Information Disclosure Statement filed Apr. 22, 2008).
He et al., 1997, "The 34.5 Protein of Herpes Simplex Virus 1 Complexes With Protein Phosphatase 1α to Dephosphorylate the α subunit of the eukaryotic translation initiation factor 2 and preclude the shutoff of protein synthesis by double stranded RNA-activated protein kinase", Proc. Natl. Acad. Sci. USA 94:843-8.
Hengel et al., 2005, "Viruses know it all: New insights into IFN networks," Trends in Immunology 26:396-401.
Hjelle et al., 2002, "Vaccines against hantaviruses," Expert Reviews of Vaccines 1:373-384.
Hoffmann et al. "A DNA transfection system for generation of influenza A from eight plasmids," 2000, Proc. Natl. Acad. Sci. USA 97:6108-6113.
Hevey et al., 2002, "Marburg virus vaccines: comparing classical and new approaches," Vaccine 20:586-593.
Holmquist et al., 1979, "Affinity chromatography of influenza virus on immobilized alpha and beta-ketosides of neuraminic acid derivatives" in Acta Pathol Microb. Scand [B]; 87B(2):129-35 (Abstract Only).
Ito, T., J. N. S. S. Couceiro, S. Kelm, L. G. Baum, S. Krauss, M. R. Castrucci, I. Donatelli, H. Kida, J. C. Paulson, R. G. Webster, and Y. Kawaoka. 1998. Molecular basis for the generation in pigs of influenza A viruses with pandemic potential. J. Virol. 72:7367-7373.
Khiabanian et al., 2009, "Reassortment patterns in swine influenza viruses," PLoS One, 4:e7366.
Kochs et al., 2007, "Multiple anti-interferon actions of the influenza A virus NS1 protein," J Virol. Jul;81(13):7011-21.

(56) References Cited

OTHER PUBLICATIONS

Komatsu et al., 2000, "Sendai Virus Blocks Alpha Interferon Signaling to Signal Transducers and Activators of Transcription", J. Virology, 74(5): 2477-2480.
Krishnan et al., 1997, "Kinase-deficient forms of Jak1 and Tyk2 inhibit interferon alpha signaling in a dominant manner." in Eur. J. Biochem.; 247:298-305.
Krystal, et al., 1983, "Sequential mutations in the NS genes of influenza virus field strains." in J. Virol.; 45(2):547-54.
Lapidus, 1969, "Purification and Concentration of Influenza Types A and B by Chromatography on Calcium Phosphate." in Appl. Microb.; 17(4):504-6.
Li H et al., 2004, "Interspecies transmission and molecular evolution of swine influenza virus," Chinese Journal of Veterinary Science, 24:304-306 (with English-language summary).
Li & Rhode, 1990, "Mutation of lysine 405 to serine in the parvovirus H-1 NS1 abolishes its functions for viral DNA replication, late promoter trans activation, and cytotoxicity," J. Virol 10:4654-4660.
Lucas WT, et al., 1988, "Characterization of a unique protein produced by influenza A virus recoverd from a long-term persistent infection." Virology. 166(2):620-3 (Abstract previously submitted as reference C56 in Information Disclosure Statement filed Apr. 22, 2008).
Mibayashi et al., 2007, "Inhibition of retinoic acid-inducible gene I-mediated induction of beta interferon by the NS1 protein of influenza A virus. J Virol.," Jan;81(2):514-24.
Naniche et al., 2000, "Evasion of Host Defenses by Measles Virus: Wild Type Measles Virus Infection Interferes with Induction of Alpha/Beta Interferon Production", J. Virology, 74(16): 7478-7484.
Neumann et al., 1999, "Generation of influenza A viruses entirely from cloned cDNAs." in Proc. Natl. Acad Sci USA; 96:9345-50.
Palese et al., 1999, "Learning from our foes: a novel vaccine concept for influenza virus." Arch Virol Suppl. 15:131-8.
Pansaert M, Ottis K, Vandeputte J, Kaplan M M, Bachmann P A. Evidence of natural transmission of influenza A virus from wild ducks to swine and its potential importance for man. Bull W H O. 1996;59:75-78.
Perez et al., 2003, "Land-based birds as potential disseminators of avian/mammalian reassortant influenza A viruses," Avian Diseases 47:1114-1117.
Qian et al., 1995, "An amino-terminal polypeptide fragment of the influenza virus NS1 protein possesses specific RNA-binding activity and largely helical backbone structure.", RNA 1:948-56.
Quinlivan et al., 2005, "Attenuation of equine influenza viruses through truncations of the NS1 protein." J Virol. Jul;79(13):8431-9.
Restifo et al., 1998, "Transfectant influenza A viruses are effective recombinant immunogens in the treatment of experimental cancer.", Virology 249:89-97.
Richt & Garcia-Sastre, 2009, "Attenuated influenza virus vaccines with modified NS1 proteins," Current Topics in Microbiology and Immunology 333:177-195.
Richt et al., 2006, "Vaccination of pigs against swine influenza viruses by using an NS1-truncated modified live-virus vaccine." J Virol. Nov;80(22):11009-18.
Rogers G N, Paulson J C. Receptor determinants of human and animal influenza virus isolates: differences in receptor specificity of the H3 hemagglutinin based on species of origin. Virology. 1983;127:361-373.
Schlender et al., 2000, "Bovine Respiratory Syncytial Virus Nonstructural Proteins NS1 and NS2 Cooperatively Antagonize Alpha/Beta Interferon-Induced Antiviral Response", J. of Virology 74(18):8234-8242.
Scholtissek et al., 1998, "Influenza in pigs and their role as the intermediate host," Ch. 13 in K. G. Nicholson, R. G. Webster, A. J. Hay (ed.), Textbook of influenza, Blackwell Science, Oxford, United Kingdom, pp. 137-145.
Scholtissek, 1994, "Source for influenza pandemics." in Eur J. Epidemiol.; 10:455-8.
Schultz U, Fitch W M, Ludwig S, Mandler J, Scholtissek C. Evolution of pig influenza viruses. Virology. 1991;183:61-73.

Seno et al., 1990, "Enhancing Effect of Centrifugation on Isolation of Influenza Virus from Clinical Specimens." J Clin. Microb. 28(7):1669-1670.
Shope RE, 1951, "The provocation of masked swine influenza virus by infection with human influenza virus," Tijdschrift Voor Diergeneeskunde 76:414-420.
Shu et al., 1994, "Evidence for interspecies transmission and reassortment of influenza A viruses in pigs in southern China." in Virol.; 202:825-33.
Solorzano et al., 2005, "Mutations in the NS1 protein of swine influenza virus impair anti-interferon activity and confer attenuation in pigs." J Virol. Jun;79(12):7535-43.
Stark et al., 1998, "How Cells Respond to Interferons", in Annu. Rev. Biochem.; 67:227-64.
Talon et al., 2000, "Activation of Interferon Regulatory Factor 3 Is Inhibited by the Influenza A Virus NS1 Protein", J. of Virology, 74(17): 7989-7996.
Taniguchi et al., 1996, "Nondefective rotavirus mutants with an NSP1 gene which has a deletion of 500 nuclcotides, including a cysteine-rich zinc finger motif-encoding region (nuclcotides 156 to 248), or which has a nonsense codon at nucleotides 153 to 155," Journal of Virology 70:4125-4130.
Veselov et al., 1984, "Isolation of preparative amounts of influenza virus hemagglutinin by an affinity chromatographic method." Vopr Virusol 29(1):93-7 (Abstract Only).
Vincent et al., 2007, "Efficacy of intranasal administration of a truncated NS1 modified live influenza virus vaccine in swine," Vaccine 25:7999-8009.
Wang et al., 2002, "Functional replacement of the carboxy-terminal two-thirds of the influenza A virus NS1 protein with short heterologous dimerization domains." J Virol. Dec;76(24):12951-62.
Wang et al., 2000, "Influenza A Virus NS1 Protein Prevents Activation of NF-KB and Induction of Alpha/Beta Interferon", J. of Virology 74(24): 11566-11573.
Weber et al., 2004, "Inverse interference: How viruses fight the interferon system," Viral Immunology 17:498-525.
Webster & Thomas, 1993, "Efficacy of equine influenza vaccines for protection against A/Equine/Jilin/89 (H3N8)—a new equine influenza virus," Vaccine 11:987-993.
Wressnigg et al., 2009, "Influenza B mutant viruses with truncated NS1 proteins grow efficiently in Vero cells and are immunogenic in mice," Journal of General Virology 90:366-374.
Young et al., 2000, "Paramyxoviridae Use Distinct Virus Specific Mechanisms to Circumvent the Interferon Response", Virology, 269:383-390.
Zhu et al., 2008, "A naturally occurring deletion in its NS1 gene contributes to the attenuation of an H5N1 swine influenza virus in chickens," Journal of Virology 82:220-228.
Written Opinion PCT/US99/13139, dated Jun. 14, 2000.
Written Opinion PCT/US99/13142, dated May 3, 2000.
Written Opinion PCT/US99/13144, dated Jul. 25, 2000.
Written Opinion PCT/US05/19383, dated Oct. 11, 2006.
Written Opinion PCT/US05/19382, dated Sep. 28, 2006.
International Search Report PCT/US99/13139, dated Oct. 28, 1999.
International Search Report PCT/US99/13142, dated Oct. 21, 1999.
International Search Report PCT/US99/13144, dated Oct. 21, 1999.
International Search Report PCT/US01/11543, dated Mar. 5, 2002.
International Search Report PCT/US05/19382, dated Oct. 25, 2006.
International Search Report PCT/US05/19383, dated Nov. 8, 2006.
International Preliminary Examination Report PCT/US01/11543, dated Mar. 5, 2002.
International Preliminary Examination Report PCT/US99/13139, dated Sep. 12, 2000.
International Preliminary Examination Report PCT/US99/13142, dated Aug. 9, 2000.
International Preliminary Examination Report PCT/US99/13144, dated Nov. 28, 2000.
International Preliminary Report on Patentability PCT/US01/11543, dated Mar. 5, 2002.
International Preliminary Report on Patentability PCT/US05/19382, dated Dec. 28, 2006.
International Preliminary Report on Patentability PCT/US05/19383, dated Aug. 21, 2007.

(56) References Cited

OTHER PUBLICATIONS

Supplementary Partial European Search Report EP 99 92 7440, dated Jun. 14, 2001.
Supplementary European Search Report EP 99 92 7443, dated Oct. 30, 2002.
Supplementary Partial European Search Report EP 99 92 7445, dated Nov. 3, 2004.
Supplementary European Search Report EP 05 85 6778, dated Dec. 9, 2009.
Supplementary European Search Report EP 05 85 6779, dated Feb. 16, 2009.
U.S. Appl. No. 09/332,288: Notice of Allowance, dated Aug. 6, 2003.
U.S. Appl. No. 09/332,288: Amendment Under 37 C.F.R. § 1.116, dated Jul. 21, 2003.
U.S. Appl. No. 09/332,288: Office Action, dated Feb. 21, 2003.
U.S. Appl. No. 09/332,288: Amendment Under 37 C.F.R. § 1.111, dated Dec. 4, 2002.
U.S. Appl. No. 09/332,288: Office Action, dated Jun. 4, 2002.
U.S. Appl. No. 09/332,288: Examiner's Amendment, dated May 31, 2002.
U.S. Appl. No. 09/332,288: Amendment Under 37 C.F.R. § 1.111, dated Mar. 7, 2002.
U.S. Appl. No. 09/332,288: Office Action, dated Nov. 7, 2001.
U.S. Appl. No. 09/332,288: Amendment Under 37 C.F.R. § 1.111, dated Aug. 22, 2001.
U.S. Appl. No. 09/332,288: Office Action, dated Feb. 22, 2001.
U.S. Appl. No. 10/713,732, Notice of Allowance, dated Mar. 13, 2009.
U.S. Appl. No. 10/713,732, Amendment Under 37 C.F.R. § 1.111, dated Dec. 2, 2008.
U.S. Appl. No. 10/713,732, Office Action dated Jul. 2, 2008.
U.S. Appl. No. 10/713,732, Amendment Under 37 C.F.R. § 1.111, dated Apr. 11, 2008.
U.S. Appl. No. 10/713,732, Interview Summary dated Oct. 19, 2007.
U.S. Appl. No. 10/713,732, Office Action dated May 15, 2007.
U.S. Appl. No. 10/713,732, Amendment Under 37 C.F.R. § 1.111, dated Mar. 23, 2007.
U.S. Appl. No. 10/713,732, Office Action dated Oct. 24, 2006.
U.S. Appl. No. 09/332,286: Notice of Allowance dated Jan. 17, 2003.
U.S. Appl. No.09/332,286: Amendment Under 37 C.F.R. § 1.116, dated Aug. 12, 2002.
U.S. Appl. No. 09/332,286: Office Action, dated Feb. 13, 2002.
U.S. Appl. No. 09/332,286: Amendment Under 37 C.F.R. § 1.111, dated Nov. 8, 2001.
U.S. Appl. No. 09/332,286: Office Action, dated May 8, 2001.
U.S. Appl. No. 09/332,286: Office Action, dated Dec. 6, 2000.
U.S. Appl. No. 09/332,286: Amendment Under 37 C.F.R. § 1.116, dated Nov. 24, 2000.
U.S. Appl. No. 09/332,286: Office Action, dated May 23, 2000.
U.S. Appl. No. 09/332,286: Amendment Under 37 C.F.R. § 1.111, dated Mar. 6, 2000.
U.S. Appl. No. 09/332,286: Office Action, dated Oct. 4, 1999.
U.S. Appl. No. 09/724,419: Notice of Allowance, dated May 27, 2004.
U.S. Appl. No. 09/724,419: Amendment Under 37 C.F.R. § 1.116, dated Feb. 26, 2004.
U.S. Appl. No. 09/724,419: Office Action, dated Aug. 26, 2003.
U.S. Appl. No. 09/724,419: Amendment Under 37 C.F.R. § 1.111, dated Jun. 11, 2003.
U.S. Appl. No. 09/724,419: Office Action, dated Feb. 11, 2003.
U.S. Appl. No. 09/724,419: Amendment Under 37 C.F.R. § 1.111, dated Dec. 31, 2002.
U.S. Appl. No. 09/724,419: Office Action, dated Jul. 2, 2002.
U.S. Appl. No. 09/724,419: Amendment Under 37 C.F.R. § 1.111, dated Apr. 19, 2002.
U.S. Appl. No. 09/724,419: Office Action, dated Dec. 19, 2001.
U.S. Appl. No. 10/945,718: Notice of Allowance, dated Oct. 16, 2008.
U.S. Appl. No. 10/945,718: Amendment Under 37 C.F.R. § 1.111, dated Apr. 7, 2008.
U.S. Appl. No. 10/945,718: Office Action, dated Oct. 5, 2007.
U.S. Appl. No. 10/945,718: Amendment Under 37 C.F.R. § 1.111, dated Nov. 28, 2006.
U.S. Appl. No. 10/945,718: Office Action, dated Aug. 29, 2006.
U.S. Appl. No. 10/945,718: Reply Under 37 C.F.R. § 1.111, dated May 10, 2006.
U.S. Appl. No. 10/945,718: Office Action, dated Jan. 10, 2006.
U.S. Appl. No. 10/945,718: Reply Under 37 C.F.R. § 1.111, dated Oct. 24, 2005.
U.S. Appl. No. 10/945,718: Office Action, dated Jun. 22, 2005.
U.S. Appl. No. 12/364,243, Office Action dated Mar. 17, 2010.
U.S. Appl. No. 12/364,243, Amendment dated Aug. 17, 2010.
U.S. Appl. No. 12/364,243, Office communication dated Oct. 27, 2010.
U.S. Appl. No. 12/364,243, Response to Office communication dated Nov. 29, 2010.
U.S. Appl. No. 09/332,287: Notice of Allowance, dated May 28, 2002.
U.S. Appl. No. 09/332,287: Office Action, dated Apr. 15, 2002.
U.S. Appl. No. 09/332,287: Supplemental Amendment Under 37 C.F.R. § 1.116, dated Apr. 12, 2002.
U.S. Appl. No. 09/332,287: Supplemental Amendment Under 37 C.F.R. § 1.116, dated Apr. 10, 2002.
U.S. Appl. No. 09/332,287: Amendment Under 37 C.F.R. § 1.116, dated Mar. 25, 2002.
U.S. Appl. No. 09/332,287: Office Action, dated Oct. 25, 2001.
U.S. Appl. No. 09/332,287: Amendment Under 37 C.F.R. § 1.111, dated Sep. 14, 2001.
U.S. Appl. No. 09/332,287: Office Action, dated Mar. 14, 2001.
U.S. Appl. No. 10/314,569: Notice of Allowance, dated Oct. 20, 2004.
U.S. Appl. No. 10/314,569: Amendment Under 37 C.F.R. § 1.116, dated Sep. 17, 2004.
U.S. Appl. No. 10/314,569: Office Action dated Apr. 20, 2004.
U.S. Appl. No. 10/314,569: Amendment Under 37 C.F.R. § 1.111, dated Jan. 26, 2004.
U.S. Appl. No. 10/314,569: Office Action dated Aug. 26, 2003.
U.S. Appl. No. 11/628,292: Preliminary Amendment Under 37 C.F.R. § 1.115, dated Nov. 30, 2006.
U.S. Appl. No. 11/628,292: Second Preliminary Amendment Under 37 C.F.R. § 1.115, dated Feb. 6, 2008.
U.S. Appl. No. 11/628,292: Restriction Requirement, dated Dec. 17, 2008.
U.S. Appl. No. 11/628,292: Response to Restriction Requirement Under 37 C.F.R. § 1.143, dated Feb. 17, 2009.
U.S. Appl. No. 11/628,292: Non-Final rejection, dated May 21, 2009.
U.S. Appl. No. 11/628,292: Response to Non-Final rejection Under 37 C.F.R. § 1.111, Nov. 23, 2009.
U.S. Appl. No. 11/628,292: Office Action, dated Feb. 19, 2010.
U.S. Appl. No. 11/628,292: Amendment dated Aug. 12, 2010.
U.S. Appl. No. 11/884,401, Office Action date Jun. 10, 2009.
U.S. Appl. No. 11/884,401, Amendment dated Dec. 10, 2009.
U.S. Appl. No. 11/884,401, Office Action dated Mar. 3, 2010.
U.S. Appl. No. 11/884,401, Amendment dated Sep. 2, 2010.
European patent application No. 99927445: Response to Invitation pursuant to Article 94(3) EPC and Rule 71(1) EPC, dated May 10, 2010.
European patent application No. 99927445: Invitation pursuant to Article 94(3) EPC and Rule 71(1) EPC, dated Nov. 9, 2009.
European patent application No. 99927445: Response to Nov. 14, 2007 Communication pursuant to Article 96(2) EPC, dated May 26, 2008.
European patent application No. 99927445: Communication pursuant to Article 96(2) EPC, dated Nov. 14, 2007.
European patent application No. 99927445: Response to May 26, 2006 Communication pursuant to Article 96(2) EPC, dated Dec. 5, 2006.
European patent application No. 99927445: Communication pursuant to Article 96(2) EPC, dated May 26, 2006.
European patent application No. 99927445: Response to Mar. 21, 2005 Communication pursuant to Article 96(2) EPC, dated Sep. 30, 2005.

(56) References Cited

OTHER PUBLICATIONS

European patent application No. 99927445: Communication pursuant to Article 96(2) EPC, dated Mar. 21, 2005.
European patent application No. 99927443, Communication Pursuant to Article 96(2) EPC, dated May 22, 2003.
European patent application No. 99927443, Reply to Communication Pursuant to Article 96(2) EPC, dated Sep. 22, 2003.
European patent application No. 99927443, Communication Pursuant to Article 96(2) EPC, dated Dec. 1, 2003.
European patent application No. 99927443, Response to Communication Pursuant to Article 96(2) EPC, dated Feb. 9, 2004.
European patent application No. 99927443, Communication Pursuant to Article 96(2) EPC, dated Mar. 30, 2004.
European patent application No. 99927443, Response to Communication Pursuant to Article 96(2) EPC, dated Jul. 30, 2004.
European patent application No. 99927443, Communication Pursuant to Article 96(2) EPC and Rule 51(2) EPC, dated Aug. 30, 2004.
European patent application No. 99927443, Response to Communication Pursuant to Article 96(2) EPC and Rule 51(2) EPC, dated Oct. 26, 2004.
European patent application No. 99927443, Communication Pursuant to Article 96(2) EPC, dated Dec. 2, 2004.
European patent application No. 99927443, Communication Pursuant to Article 96(2) EPC, dated Jun. 6, 2005.
European patent application No. 99927443, Communication Pursuant to Article 96(2) EPC, dated Jul. 14, 2005.
European patent application No. 99927443, Response to Communication Pursuant to Article 96(2) EPC, dated Jan. 23, 2006.
European patent application No. 99927443, Communication under Rule 51(4) EPC, dated Jun. 12, 2006.
European Patent Application No. EP 05 856 778.5, Communication pursuant to Article 94(3) EPC, dated Apr. 7, 2010.
European Patent Application No. EP 05 856 778.5, Response to Communication pursuant to Article 94(3) EPC, dated Oct. 15, 2010.
European Patent Application No. EP 05 856 779.3, Communication pursuant to Article 94(3) EPC, dated Oct. 6, 2010.
European Patent Application No. EP 05 856 779.3, Response to Communication pursuant to Article 94(3) EPC, dated Apr. 15, 2011.
U.S. Appl. No. 11/884,401; Office Action, dated Mar. 31, 2011.
U.S. Appl. No. 11/884,401; Response to Notice of Non-Compliant Amendment (37 C.F.R. § 1.121), dated Jan. 24, 2011.
U.S. Appl. No. 12/364,243; Office Action dated Feb. 16, 2011.
Garcia-Sastre et al., 1994, "Introduction of foreign sequences into the genome of influenza A virus," Dev Biol Stand. 82:237-46.
U.S. Appl. No. 12/364,243, Reply Under 37 C.F.R. § 1.114, dated Jul. 18, 2011.
U.S. Appl. No. 11/884,401, Office communication with Notice of Allowability, dated Aug. 25, 2011.
U.S. Appl. No. 11/884,401, Notice of Allowance, dated Aug. 18, 2011.
U.S. Appl. No. 11/628,292, Notice of Allowance and Examiner-Initiated Interview Summary, dated Jul. 1, 2011.
U.S. Appl. No. 11/628,292, Amendment under 37 C.F.R. § 1.111, dated Apr. 15, 2011.
U.S. Appl. No. 11/628,292, Office Action, dated Nov. 15, 2010.
European Patent Application No. EP 05 856 778.5, Communication pursuant to Article 94(3) EPC, dated Jun. 28, 2011.
Aoki et al., 1996, "Differential sensitivity of two related viruses, Newcastle disease virus and Sendai virus, to interferon in mouse Had-2 cells selective inhibition of translation of NDV mRNA." Arch Virol., 141(10):1847-62.
Arvin et al., 2006, "New viral vaccines", Virology 344:240-9.
Baez et al., 1980, "Complete nucleotide sequence of the influenza A/PR/8/34 virus NS gene and comparison with the NS genes of the A/Udorn/72 and A/FPV/Rostock/34 strains", Nucleic Acids Res. 8(23):5845-58.
Beatrice et al., 1980, "Immunogenicity in mice of temperature-sensitive mutants of vesicular stomatitis virus: early appearance in bronchial secretions of an interferon-like inhibitor", J Gen Virol. 47:529-33.

Belardelli, 1996, "The neglected role of type I interferon in the T-cell response: implications for its clinical use", Immunol. Today 17(8):369-72.
Briscoe et al., 1996, "Kinase-negative mutants of JAK1 can sustain interferon-gamma-inducible gene expression but not an antiviral state", EMBO J. 15:799-809.
Buonagurio et al., 1986, "Evolution of human influenza A viruses over 50 years: rapid, uniform rate of change in NS gene", Science. 232(4753):980-2.
Butterfteld et al., 1978, "Vaccination for fowl plague", Am J Vet Res. 39(4):671-4.
Chang et al., 1992, "The E3L gene of vaccinia virus encodes an inhibitor of the interferon-induced, double-stranded RNA-dependent protein kinase", Proc. Natl. Acad. Sci USA 89:4825-4829.
Chen et al., 1999, "Influenza A virus NS1 protein targets poly(A)-binding protein II of the cellular 3'-end processing machinery", EMBO J. 18(8):2273-83.
Constantinescu et al., 1995, "Expression and signaling specificity of the IFNAR chain of the type I interferon receptor complex", Proc. Natl. Acad. Sci. USA 92:10487-91.
Cossins et al., 1993, "Precise Prediction of a Kk-Restricted Cytotoxic T Cell Epitope in the NS1 Protein of Influenza Virus Using an MHC Allele-Specific Motif", Virology 193(1):289-95.
Crowe, 1998, "Immune responses of infants to infection with respiratory viruses and live attenuated respiratory virus candidate vaccines", Vaccine 16(14/15):1423-32.
Cruse et al., Eds. 2003, "Knockout Gene" in Illustrated Dictionary of Immunology, 2nd Edition, CRC Press p. 367.
De La Luna et al., 1995, "Influenza virus NS1 protein enhances the rate of translation initiation of viral mRNAs", J Virol 69(4):2427-33.
Da Silva et al., 2006, "Vaccines under development; group B *Streptococcus*, herpes-zoster, HIV, malaria and dengue", Jornal de Pediatria 82 (Suppl 3):115-24.
Desmyter et al., 1968, "Defectiveness of interferon production and of rubella virus interference in a line of African green monkey kidney cells (Vero)", J Virol. 2(10):955-61.
Diaz et al., 1988, "Homozygous deletion of the alpha- and beta 1-interferon genes in human leukemia and derived cell lines", Proc Natl Acad Sci U S A. 85(14):5259-63.
Dulbecco et al., Eds. 1988, "Multiplication and Genetics of Animal Viruses.", Virology Ch. 48 pp. 77-79.
Durbin et al., 1996, "Targeted disruption of the mouse Stat1 gene results in compromised innate immunity to viral disease", Cell. 84(3):443-50.
Efferson et al., 2006, "Prostate tumor cells infected with a recombinant influenza virus expressing a truncated NS1 protein activate cytolytic CD8+ cells to recognize noninfected tumor cells.", J Virol. 80(1):383-94.
Egorov et al., 1994, "[The NS gene—a possible determinant of apathogenicity of a cold-adapted donor of attenuation A /Leningrad/ 134/47/57 and its reassortants]", Vopr Virusol. 39(5):201-5. Russian.
Egorov et al., 1998, "Transfectant influenza A viruses with long deletions in the NS1 protein grow efficiently in Vero cells", J Virol. 72(8):6437-41.
Egorov et al., 1997, "Generation of influenza A transfectant viruses containing deletions of the carboxyl-terminal part of the NS1 protein", Emergence and Re-emergence of Negative Strand Viruses, Tenth International Conference on Negative Strand Viruses. Sep. 21-26, Dublin, Ireland. Abstract No. 108, p. 104.
Egorov et al., 1997, "Generation of Influenza A Transfectant Viruses Containing Deletions in the NS1 Protein", Institute of Applied Microbiology, Emergence and Re-emergence of Negative Strand Viruses, Tenth International Conference on Negative Strand Viruses. Sep. 21-26, Dublin, Ireland. Poster.
Enami et al., 1991, "An influenza virus containing nine different RNA segments", Virology 185(1):291-8.
Enami et al., 1991, "High-efficiency formation of influenza virus transfectants", J Virol. 65(5):2711-3.
Enami et al., 1994, "Influenza virus NS1 protein stimulates translation of the M1 protein", J Virol. 68(3):1432-7.
Fenner et al., 1974, The Biology of Animal Viruses, in $2^{nd}$ Ed. New York: Academic Press pp. 42-43.

(56) References Cited

OTHER PUBLICATIONS

Ferko et al., 2004, "Immunogenicity and protection efficacy of replication-deficient influenza A viruses with altered NS1 genes.", J Virol. 78(23):13037-45.
Finn, 2003, "Cancer vaccines: between the idea and the reality." Nature 3:630-41.
Fodor et al., 1998, "Attenuation of influenza A virus mRNA levels by promoter mutations", J Virol. 72(8):6283-90.
Fortes et al., 1994, "Influenza virus NS1 protein inhibits pre-mRNA splicing and blocks mRNA nucleocytoplasmic transport", EMBO J. 13(3):704-12.
Garcia-Sastre et al., 1998, "Influenza A virus lacking the NS1 gene replicates in interferon-deficient systems", Virology 252(2):324-30.
Garcia-Sastre et al., 1998, "The role of interferon in influenza virus tissue tropism", J Virol. 72(11):8550-8.
Garcia-Sastre, 2001, "Inhibition of interferon-mediated antiviral responses by influenza A viruses and other negative-strand RNA viruses." Virology 279(2):375-84.
Goodpasture et al., 1934, "The cultivation of vaccine and other viruses in the chorioallantoic membrane of chick embryos", Science. 74(1919):371-2.
Hackett et al., 1992, "Influenza virus infection elicits class II major histocompatibility complex-restricted T cells specific for an epitope identified in the NS1 non structural protein." J. of Gen. Virology 73:1339-43.
Haller et al., 1986, "Genetic resistance to influenza virus in wild mice", Curr Top Microbiol Immunol. 127:331-7.
Haller et al., 1980, "Host gene influences sensitivity to interferon action selectively for influenza virus", Nature. 283(5748):660-2.
Haller, 1981, "Inborn resistance of icc to orthomyxoviruscs", Curr Top Microbiol Immunol. 92:25-52.
Hamzawt et al., 1981, "Antigenicity in hamsters of inactivated vaccines prepared from recombinant influenza viruses.", J Hyg (Lond). 87(3):453-64.
Hatada et al., 1992, "Binding of influenza A virus NS1 protein to dsRNA in vitro", J Gen Virol. 73 ( Pt 12):3325-9.
Katinger et al., 1997, "Attenuated Influenza Virus as a Vector for Mucosal Immunization Against HIV-1", Vaccine 315-9.
Krug et al., 1975, "Studies on the intranuclear localization of influenza virus-specific proteins", Virology 64: 378-87.
Krug, 1995, "Chapter 8. Unique Functions of the NS1 Protein" Textbook of Influenza, Nicholson et al. (eds.), pp. 82-92.
Krystal, et al., 1983, "Sequential mutations in the NS genes of influenza virus field strains." in J. Virol.; 45(2):547-54. (Abstract only).
Kuwano et al., 1988, "HA2 Subunit of Influenza A H1 and H2 Subtype Viruses Induces a Protective Cross Reactive Cytotoxic T Lymphocyte Response", J. Immunol. 140:1264-8.
Kuwano et al., 1990, "Cross reactive protection against influenza A virus infections by an NS1-specific CTL clone", Immunochemistry 178:174-9.
Lewis, 1985, "Induction of anti-viral activity and specific enzymes in cell-lines derived from interferon-resistant, thymidine kinase deficient mouse L-929 cells", Prog Clin Biol Res. 202:325-32.
Li et al., 1992, "Mutational analysis of the promoter required for influenza virus virion RNA synthesis", J Virol. 66(7):4331-8.
Li et al., 1994, "Characterization of the polyadenylation signal of influenza virus RNA", J Virol. 68(2):1245-9.
Loh et al., 1994, "Mutant cell lines unresponsive to alpha/beta and gamma interferon are defective in tyrosine phosphorylation of ISGF-3-alpha components", Mol. Cell. Biol. 14:2170-9.
Lu et al., 1994, "The influenza virus NS1 protein: a novel inhibitor of pre-mRNA splicing", Genes Dev. 8(15):1817-28.
Lu et al., 1995, "Binding of the influenza virus NS1 protein to double-stranded RNA inhibits the activation of the protein kinase that phosphorylates the eIF-2 translation initiation factor", Virology. 214(1):222-8.
Lucas, et al., 1988, "Characterization of a unique protein produced by influenza A virus recovered from a long-term persistent infection." Virology 166(2):620-3. (Abstract only cited).

Luo et al., 1991, "The polyadenylation signal of influenza virus RNA involves a stretch of uridines followed by the RNA duplex of the panhandle structure", J Virol. 65(6):2861-7.
Luytjes et al., 1989, "Amplification, expression, and packaging of foreign gene by influenza virus", Cell. 59(6):1107-13.
Maassab et al., 1983, "Characterization of an Influenza A Host Range Mutant", Virology 130:342-50.
Maramorosh et al., 1967, Methods in Virology, Academic Press, New York vol. 1, chapter 6, pp. 178-216.
Marcus et al., 1994, "Interferon induction: regulation by both virus and cell." Hokkaido Igaku Zasshi 69(6):1320-31.
Marion et al., 1997, "The N-terminal half of influenza virus NS1 protein is fully active both in mRNA nuclear retention and enhancement of translation", in Emergence and Re-emergence of Negative Strand Viruses, Tenth International Conference on Negative Strand Viruses., Dublin, Ireland. Abstract No. 240, p. 170.
Marion et al., 1997, "The N-terminal half of the influenza virus NS1 protein is sufficient for nuclear retention of mRNA and enhancement of viral mRNA translation", Nucleic Acids Res. 25(21):4271-7.
Mebatsion et al., 2001, "A recombinant Newcastle disease virus with low-level V protein expression is immunogenic and lacks pathogenicity for chicken embryos.", J Virol. 5(1):420-8.
Meraz et al., 1996, "Targeted disruption of the Stat1 gene in mice reveals unexpected physiologic specificity in the JAK-STAT signaling pathway", Cell. 84(3):431-42.
MMWR Weekly, 2007, "Progress Toward Poliomyelitis Eradication—Nigeria, 2005-2006" www.cdc.gov/mmwr/preview/mmwrhtml/mm5612a3.htm Mar. 30, 56(12):278-81.
Morahan et al., 1970, "Age-related cellular resistance of the chicken embryo to viral infections. I. Interferon and natural resistance to myxoviruses and vesicular stomatitis virus.", J Infect Dis 121(6):615-23.
Mosca et al., 1986, "Transcriptional and posttranscriptional regulation of exogenous human beta interferon gene in simian cells defective in interferon synthesis", Mol Cell Biol. 6(6):2279-83.
Murphy et al., 1996, "Orthomyxoviruses" in Fields Virology, Lippincott-Raven P.A., pp. 1397-1445.
Muster et al., 1991, "An influenza A virus containing influenza B virus 5' and 3' noncoding regions on the neuraminidase gene is attenuated in mice", Proc Natl Acad Sci U S A. 88(12):5177-81.
Mwau et al., 2003, "A review of vaccines for HIV prevention." J. Gene. Med. 5:3-10.
Nemeroff et al., 1997, "Unique interactions of the influenza virus NS 1 protein with host cell nuclear functions", in Emergence and Re-emergence of Negative Strand Viruses, Tenth International Conference on Negative Strand Viruses., Dublin, Ireland. Abstract No. 229, p. 164.
Nemeroff et al., 1998, "Influenza virus NS1 protein interacts with the cellular 30 kDa subunit of CPSF and inhibits 3' end formation of cellular pre-mRNAs", Mol Cell. 1(7):991-1000.
Norton et al., 1987, "Infectious influenza A and B virus variants with long carboxyl terminal deletions in the NS1 polypeptides" Virology 156(2):204-13.
Orkin et al., 1995, Report and recommendations of the panel to assess the NIH investment in research on gene therapy. National Institutes of Health, Bethesda, MD.
Park et al. ,2003, "Newcastle disease virus (NDV)-based assay demonstrates interferon-antagonist activity for the NDV V protein and the Nipah virus V, W, and C proteins." J Virol. 77(2):1501-11.
Park et al., 1995, "Translational control by influenza virus. Identification of cis-acting sequences and trans-acting factors which may regulate selective viral mRNA translation", J Biol Chem. 270(47):28433-9.
Parvin et al., 1983, "Nonsense mutations affecting the lengths of the NS1 nonstructural proteins of influenza A virus isolates" Virology 128(2):512-7.
Perry et al., 1993, "Transgenesis in chickens" Transgenic Res. 2(3):125-33.
Piccone et al., 1993, "Mutational analysis of the influenza virus vRNA promoter", Virus Res. 28(2):99-112.
Pleschka et al., 1996, "A plasmid-based reverse genetics system for influenza A virus", J Virol. 70(6):4188-92.

(56) References Cited

OTHER PUBLICATIONS

Qin et al., 1998, "Interferon-beta gene therapy inhibits tumor formation and causes regression of established tumors in immune-deficient mice", Proc Natl Acad Sci USA. 95(24):14411-6.

Qiu et al., 1994, "The influenza virus NS1 protein is a poly(A)-binding protein that inhibits nuclear export of mRNAs containing poly(A)", J Virol. 68(4):2425-32.

Qiu et al., 1995, "The influenza virus NS1 protein binds to a specific region in human U6 snRNA and inhibits U6-U2 and U6-U4 snRNA interactions during splicing", RNA. 1(3):304-16.

Qureshi et al., 1996, "Function of Stat2 protein in transcriptional activation by alpha interferon", Mol. Cell. Biol. 16:288-93.

Robert-Guroff et al., 1998, "Vaccine protection against a heterologous, non-syncytium-inducing, primary human immunodeficiency virus.", J. Virol. 72:10275-80.

Sang, 1994, "Transgenic chickens—methods and potential applications", Trends Biotechnol. 12(10):415-20.

Schuepbach et al., 1983, "Early antiviral antibody response after immunization with viral oncolysate: a powerful prognostic marker for acute myelogenous leukemia remission patients" Blood 62:616-21.

Sekellick et al., 1985, "Interferon induction by viruses. XIV. Development of interferon inducibility and its inhibition in chick embryo cells "aged" in vitro", J Interferon Res. 5(4):651-67.

Sekellick et al., 1990, "Development of the interferon system. I. In chicken cells development in ovo continues on time in vitro", Vitro Cell Dev Biol. 26(10):997-1003.

Shaw et al., 1982, "Immunologic Studies on the Influenza A Virus Nonstructural Protein NS", J. Exp. Med. 156:243-54.

Shaw et al., 1996, "Nucleocapsid protein alone is sufficient for the generation of influenza transfectants" Options for the Control of Influenza III, Brown (eds.), Hampson Webster (Elsevier Science) 433-6.

Shuman, 1991, "Production of transgenic birds", Experientia. 47(9):897-905.

Snyder et al., 1990, "A 36 Nucleotide Deletion Mutation in the Coding Region of the SN1 Gene of an Influenza A Virus RNA Segment 8 Specifies a Temperature-Dependent Host Range Phenotype", Virus Research 15:69-84.

Stern., 1996, "Chick stem cells", Curr Top Microbiol Immunol. 212:195-206.

Talon et al. ,2000, "Influenza A and B viruses expressing altered NS1 proteins: A vaccine Approach." Proc Natl Acad Sci USA 96(8):4309-14.

Tobita et al., 1990, "Nucleotide sequence and some biological properties of the NS gene of a newly isolated influenza B virus mutant which has a long carboxyl terminal deletion in the NS1 protein", Virology 174(1):314-9.

Vandermark et al., eds., 1986, The Microbes pp. 670-680.

Verma et al., 1997, "Gene therapy—promises, problems and prospects.", Nature 389(6648):239-42.

Weaver et al., 1998, "Interferon regulatory factor 3 and CREB-binding protein/p300 are subunits of double-stranded RNA-activated transcription factor DRAF1", Mol Cell Biol. 18(3):1359-68.

Wong et al., 1997, "Interferon-resistant human melanoma cells are deficient in ISGF3 components, STAT1, STAT2, and p48-ISGF3-gamma.", J. Biol. Chem. 272:28779-85.

Yang et al., 1998, "STAT3 complements defects in an interferon-resistant cell line: Evidence for an essential role for STAT3 in interferon signaling and biological activities", Proc. Natl. Acad. Sci. USA 95:5568-72.

Yannarell et al. ,1997, "Factors affecting the yield of cold-adapted influenza virus vaccine." J Virol Methods. 64(2):161-9.

Yoshida et al., 1981, "Characterization of the RNA Associated with Influenza A Cytoplasmic Inclusions and the Interaction of NS1 Protein with RNA.", Virology 110:87-97.

Young et al., 1983, "Efficient Expression of Influenza Virus NS1", Proc. Natl. Acad. Sci. 80:6105-9.

Landolt et al., 2003, "Comparison of the pathogenesis of two genetically different H3N2 influenza A viruses in pigs", J Clin Microbiol; 41(5):1936-1941.

Notice of Allowance and Fees Due of U.S. Appl. No. 12/148,798, dated Sep. 21, 2011.

U.S. Appl. No. 12/148,798, Office Action, dated Aug. 17, 2011.

U.S. Appl. No. 12/148,798, Office Action, dated Nov. 29, 2010.

Webby et al., 2000, "Evolution of swine H3N2 in influenza viruses in the United States", J Virol; 74(18):8243-8251.

ATTENUATED NEGATIVE STRAND VIRUSES WITH ALTERED INTERFERON ANTAGONIST ACTIVITY FOR USE AS VACCINES AND PHARMACEUTICALS

This application is a divisional of, and claims benefit of, U.S. application Ser. No. 12/148,798, filed Apr. 22, 2008 (issued as U.S. Pat. No. 8,057,803), which is a continuation of U.S. application Ser. No. 10/713,732, filed Nov. 14, 2003 (issued as U.S. Pat. No. 7,588,768 on Sep. 15, 2009), which is a continuation of, and claims benefit of, U.S. application Ser. No. 09/332,288, filed Jun. 11, 1999, which issued as U.S. Pat. No. 6,669,943 on Dec. 30, 2003, which is a continuation-in-part of U.S. Application Ser. No. 60/117,683 filed Jan. 29, 1999; U.S. Application Ser. No. 60/108,832, filed Nov. 18, 1998; and U.S. Application Ser. No. 60/089,103, filed Jun. 12, 1998, each of which is incorporated by reference in its entirety herein.

The work reflected in this application was supported, in part, by a grant from the National Institutes of Health, and the Government may have certain rights to the invention.

1. INTRODUCTION

The present invention relates, in general, to attenuated negative-strand RNA viruses having an impaired ability to antagonize the cellular interferon (IFN) response, and the use of such attenuated viruses in vaccine and pharmaceutical formulations. The invention also relates to the development and use of IFN-deficient systems for the selection, identification and propagation of such attenuated viruses.

In a particular embodiment, the invention relates to attenuated influenza viruses having modifications to the NS1 gene that diminish or eliminate the ability of the NS1 gene product to antagonize the cellular IFN response. The mutant viruses replicate in vivo, but demonstrate reduced pathogenicity, and therefore are well suited for use in live virus vaccines, and pharmaceutical formulations.

2. BACKGROUND OF THE INVENTION

2.1 The Influenza Virus

Virus families containing enveloped single-stranded RNA of the negative-sense genome are classified into groups having non-segmented genomes (Paramyxoviridae, Rhabdoviridae, Filoviridae and Borna Disease Virus) or those having segmented genomes (Orthomyxoviridae, Bunyaviridae and Arenaviridae). The Orthomyxoviridae family, described in detail below, and used in the examples herein, includes the viruses of influenza, types A, B and C viruses, as well as Thogoto and Dhori viruses and infectious salmon anemia virus.

The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules (seven for influenza C) of linear, negative polarity, single-stranded RNAs which encode ten polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP). Transcription and replication of the genome takes place in the nucleus and assembly occurs via budding on the plasma membrane. The viruses can reassort genes during mixed infections.

Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In other words, the eight viral RNA segments code for ten proteins: nine structural and one nonstructural. A summary of the genes of the influenza virus and their protein products is shown in Table I below.

TABLE 1

INFLUENZA VIRUS GENOME RNA SEGMENTS AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 1 | 2341 | PB2 | 759 | 30-60 | RNA transcriptase component; host cell RNA cap binding |
| 2 | 2341 | PB1 | 757 | 30-60 | RNA transcriptase component; initiation of transcription |
| 3 | 2233 | PA | 716 | 30-60 | RNA transcriptase component |
| 4 | 1778 | HA | 566 | 500 | Hemagglutinin; trimer; envelope glycoprotein; mediates attachment to cells |
| 5 | 1565 | NP | 498 | 1000 | Nucleoprotein; associated with RNA; structural component of RNA transcriptase |
| 6 | 1413 | NA | 454 | 100 | Neuraminidase; tetramer; envelope glycoprotein |
| 7 | 1027 | $M_1$ | 252 | 3000 | Matrix protein; lines inside of envelope |
|  |  | $M_2$ | 96 | ? | Structural protein in plasma membrane; spliced mRNA |

TABLE 1-continued

INFLUENZA VIRUS GENOME RNA SEGMENTS
AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 8 | 890 | $NS_1$ | 230 | | Nonstructural protein; function unknown |
| | | NEP | 121 | ? | Nuclear export protein; spliced mRNA |

[a]Adapted from R. A. Lamb and P. W. Choppin (1983), Annual Review of Biochemistry, Volume 52, 467-506.
[b]For A/PR/8/34 strain
[c]Determined by biochemical and genetic approaches
[d]Determined by nucleotide sequence analysis and protein sequencing The influenza A virus genome contains eight segments of single-stranded RNA of negative polarity, coding for one nonstructural and nine structural proteins. The nonstructural protein NS1 is abundant in influenza virus infected cells, but has not been detected in virions. NS1 is a phosphoprotein found in the nucleus early during infection and also in the cytoplasm at later times of the viral cycle (King et al., 1975, Virology 64: 378). Studies with temperature-sensitive (ts) influenza mutants carrying lesions in the NS gene suggested that the NS1 protein is a transcriptional and post-transcriptional regulator of mechanisms by which the virus is able to inhibit host cell gene expression and to stimulate viral protein synthesis. Like many other proteins that regulate post-transcriptional processes, the NS1 protein interacts with specific RNA sequences and structures. The NS1 protein has been reported to bind to different RNA species including: vRNA, poly-A, U6 snRNA, 5' untranslated region as of viral mRNAs and ds RNA (Qiu et al., 1995, RNA 1: 304; Qiu et al., 1994, J. Virol. 68: 2425; Hatada Fukuda 1992, J Gen Virol. 73:3325-9. Expression of the NS1 protein from cDNA in transfected cells has been associated with several effects: inhibition of nucleo-cytoplasmic transport of mRNA, inhibition of pre-mRNA splicing, inhibition of host mRNA polyadenylation and stimulation of translation of viral mRNA (Fortes, et al., 1994, EMBO J. 13: 704; Enami, et al, 1994, J. Virol. 68: 1432; de la Luna, et al., 1995, J. Virol. 69:2427; Lu, et al., 1994, Genes Dev. 8:1817; Park, et al., 1995, J. Biol Chem. 270, 28433; Nemeroff et al., 1998, Mol. Cell. 1:1991; Chen, et al., 1994, EMBO J. 18:2273-83).

2.2 Attenuated Viruses

Inactivated virus vaccines are prepared by "killing" the viral pathogen, e.g., by heat or formalin treatment, so that it is not capable of replication. Inactivated vaccines have limited utility because they do not provide long lasting immunity and, therefore, afford limited protection. An alternative approach for producing virus vaccines involves the use of attenuated live virus vaccines. Attenuated viruses are capable of replication but are not pathogenic, and, therefore, provide for longer lasting immunity and afford greater protection. However, the conventional methods for producing attenuated viruses involve the chance isolation of host range mutants, many of which are temperature sensitive; e.g., the virus is passaged through unnatural hosts, and progeny viruses which are immunogenic, yet not pathogenic, are selected.

A conventional substrate for isolating and growing influenza viruses for vaccine purposes are embryonated chicken eggs. Influenza viruses are typically grown during 2-4 days at 37° C. in 10-11 day old eggs. Although most of the human primary isolates of influenza A and B viruses grow better in the amniotic sac of the embryos, after 2 to 3 passages the viruses become adapted to grow in the cells of the allantoic cavity, which is accessible from the outside of the egg (Murphy, B. R., and R. G. Webster, 1996. Orthomyxoviruses p. 1397-1445. In Fields Virology. Lippincott-Raven P. A.).

Recombinant DNA technology and genetic engineering techniques, in theory, would afford a superior approach to producing an attenuated virus since specific mutations could be deliberately engineered into the viral genome. However, the genetic alterations required for attenuation of viruses are not known or predictable. In general, the attempts to use recombinant DNA technology to engineer viral vaccines have mostly been directed to the production of subunit vaccines which contain only the protein subunits of the pathogen involved in the immune response, expressed in recombinant viral vectors such as vaccinia virus or baculovirus. More recently, recombinant DNA techniques have been utilized in an attempt to produce herpes virus deletion mutants or polioviruses which mimic attenuated viruses found in nature or known host range mutants. Until 1990, the negative strand RNA viruses were not amenable to site-specific manipulation at all, and thus could not be genetically engineered.

Attenuated live influenza viruses produced thus far might not be capable of suppressing the interferon response in the host in which they replicate. Therefore, although these viruses are beneficial because they are immunogenic and not pathogenic, they are difficult to propagate in conventional substrates for the purposes of making vaccines. Furthermore, attenuated viruses may possess virulence characteristics that are so mild as to not allow the host to mount an immune response sufficient to meet subsequent challenges.

3. SUMMARY OF THE INVENTION

The present invention relates to attenuated negative strand RNA viruses having an impaired ability to antagonize the cellular IFN response, and the use of such viruses in vaccine and pharmaceutical formulations. The mutant viruses with an impaired IFN antagonist activity are attenuated—they are infectious, can replicate in vivo to provide subclinical levels of infection, and are not pathogenic. Therefore, they are ideal candidates for live virus vaccines. Moreover, the attenuated viruses can induce a robust IFN response which has other biological consequences in vivo, affording protection against subsequent infectious diseases and/or inducing antitumor responses. Therefore, the attenuated viruses can be used pharmaceutically, for the prevention or treatment of other infectious diseases, cancer in high risk individuals, and/or IFN-treatable diseases.

The negative strand RNA viruses used in accordance with the invention include both segmented and non-segmented viruses; preferred embodiments include but are not limited to influenza virus, respiratory syncytial virus (RSV), Newcastle disease virus (NDV), vesicular stomatitis virus (VSV), and parainfluenza virus (PIV). The viruses used in the invention may be selected from naturally occurring strains, variants or mutants; mutagenized viruses (e.g., generated by exposure to mutagens, repeated passages and/or passage in non-permissive hosts); reassortants (in the case of segmented viral genomes); and/or genetically engineered viruses (e.g. using the "reverse genetics" techniques) having the desired phenotype—i.e., an impaired ability to antagonize the cellular IFN response. The mutant or genetically engineered virus can be selected based on differential growth in IFN deficient systems versus IFN competent systems. For example, viruses which grow in an IFN deficient system, but not in an IFN competent system (or which grow less well in an IFN competent system) can be selected.

The attenuated virus so selected can itself be used as the active ingredient in vaccine or pharmaceutical formulations. Alternatively, the attenuated virus can be used as the vector or "backbone" of recombinantly produced vaccines. To this end, the "reverse genetics" technique can be used to engineer mutations or introduce foreign epitopes into the attenuated virus, which would serve as the "parental" strain. In this way, vaccines can be designed for immunization against strain variants, or in the alternative, against completely different infectious agents or disease antigens. For example, the attenuated virus can be engineered to express neutralizing epitopes of other preselected strains. Alternatively, epitopes of viruses other than negative strand RNA viruses can be built into the attenuated mutant virus (e.g., gp160, gp120, or gp41 of HIV). Alternatively, epitopes of non-viral infectious pathogens (e.g., parasites, bacteria, fungi) can be engineered into the virus. In yet another alternative, cancer vaccines can be prepared, e.g. by engineering tumor antigens into the attenuated viral backbone.

In a particular embodiment involving RNA viruses with segmented genomes, reassortment techniques can be used to transfer the attenuated phenotype from a parental segmented RNA virus strain (a natural mutant, a mutagenized virus, or a genetically engineered virus) to a different virus strain (a wild-type virus, natural mutant, a mutagenized virus, or a genetically engineered virus).

The attenuated viruses, which induce robust IFN responses in hosts, may also be used in pharmaceutical formulations for the prophylaxis or treatment of other viral infections, or IFN-treatable diseases, such as cancer. In this regard, the tropism of the attenuated virus can be altered to target the virus to a desired target organ, tissue or cells in vivo or ex vivo. Using this approach, the IFN response can be induced locally, at the target site, thus avoiding or minimizing the side effects of systemic IFN treatments. To this end, the attenuated virus can be engineered to express a ligand specific for a receptor of the target organ, tissue or cells.

The invention is based, in part, on the Applicants' discovery that NS1 of wild type influenza virus functions as an IFN antagonist, in that NS1 inhibits the IFN mediated response of virus-infected host cells. Viral mutants deficient for NS1 activity were found to be potent inducers of the cellular IFN response, and demonstrated an attenuated phenotype in vivo; i.e. the mutant viruses replicate in vivo, but have reduced pathogenic effects. While not intending to be bound by any theory or explanation for how the invention works, the attenuated features of the viruses of the invention are presumably due to their ability to induce a robust cellular IFN response, and their impaired ability to antagonize the host IFN response. However, the beneficial features of the attenuated viruses of the invention may not be solely attributable to the effects on the cellular interferon response. Indeed, alterations in other activities associated with NS1 may contribute to the desired attenuated phenotype.

The mutant influenza viruses with impaired IFN antagonist activity were shown to replicate in vivo generating titers that are sufficient to induce immunological and cytokine responses. For example, vaccination with attenuated influenza virus reduced viral titer in animals that were subsequently challenged with wild-type influenza virus. The attenuated influenza viruses also demonstrated antiviral and antitumor activity. Pre-infection with attenuated influenza virus inhibited replication of other strains of wild type influenza virus, and other viruses (such as Sendai virus) superinfected in embryonated eggs. Inoculation of the attenuated influenza in animals injected with tumor cells reduced the number of foci formed. Because influenza virus is known to induce a CTL (cytotoxic T lymphocyte) response, the attenuated virus is a very attractive candidate for cancer vaccines.

Mutations which diminish but do not abolish the IFN antagonist activity of the virus are preferred for vaccine formulations—such viruses can be selected for growth in both conventional and non-conventional substrates, and for intermediate virulence. In particular, the Applicants have demonstrated that an NS1 C-terminal-truncation mutant replicates to high titers in IFN deficient substrates, such as 6 and 7-day-old embryonated chicken eggs, as well as in the allantoic membrane of 10-day-old embryonated chicken eggs, the conventional substrate for influenza virus that does not permit the growth of influenza virus mutants in which the entire NS1 gene is deleted (also referred to herein as "knockout" mutants). However, replication of the NS1-C terminal truncation mutant is diminished in 12-day-old embryonated eggs. This approach allows, for the first time, the generation and identification of live attenuated negative strand RNA viruses that have altered, but not abolished, IFN antagonist activity, and that are able to grow in substrates suitable for vaccine preparation. This approach also allows for the first time, an efficient selection identification system for influenza or other viruses which contain mutations that confer altered, but not abolished, interferon antagonist activity.

The invention also relates to the use of IFN deficient systems to propagate the attenuated viruses that cannot be grown in conventional systems currently used for vaccine production. The term "IFN-deficient systems" as used herein refers to systems, e.g., cells, cell lines and animals, such as mice, chickens, turkeys, rabbits, rats, etc., which do not produce IFN or produce low levels of IFN, do not respond or respond less efficiently to IFN, and/or are deficient in the activity of antiviral genes induced by IFN. To this end, Applicants have identified or designed a number of IFN-deficient systems that can be used, including but not limited to young embryonated eggs, IFN-deficient cell lines (such as VERO cells or genetically engineered cell lines such as STAT1 knockouts). Alternatively, embryonated eggs or cell lines can be pretreated with compounds that inhibit the IFN system (including drugs, antibodies, antisense, ribozymes, etc.). Yet another embodiment involves the use of eggs deficient in the IFN system, e.g., eggs produced by STAT1 negative birds, especially fowl, including but not limited to transgenic chickens, ducks or turkeys.

4. DESCRIPTION OF THE FIGURES

FIG. 1. DelNS1 virus inhibits wild-type influenza A virus replication in eggs. Ten-day-old embryonated chicken eggs were inoculated with the indicated pfu of delNS1 virus. Eight hours later, the eggs were infected with $10^3$ pfu of WSN virus. After two days of incubation at 37° C., the allantoic fluid was harvested and WSN virus titers were determined by plaque assay in MDBK cells. Results are the average of two eggs.

Figure 2:
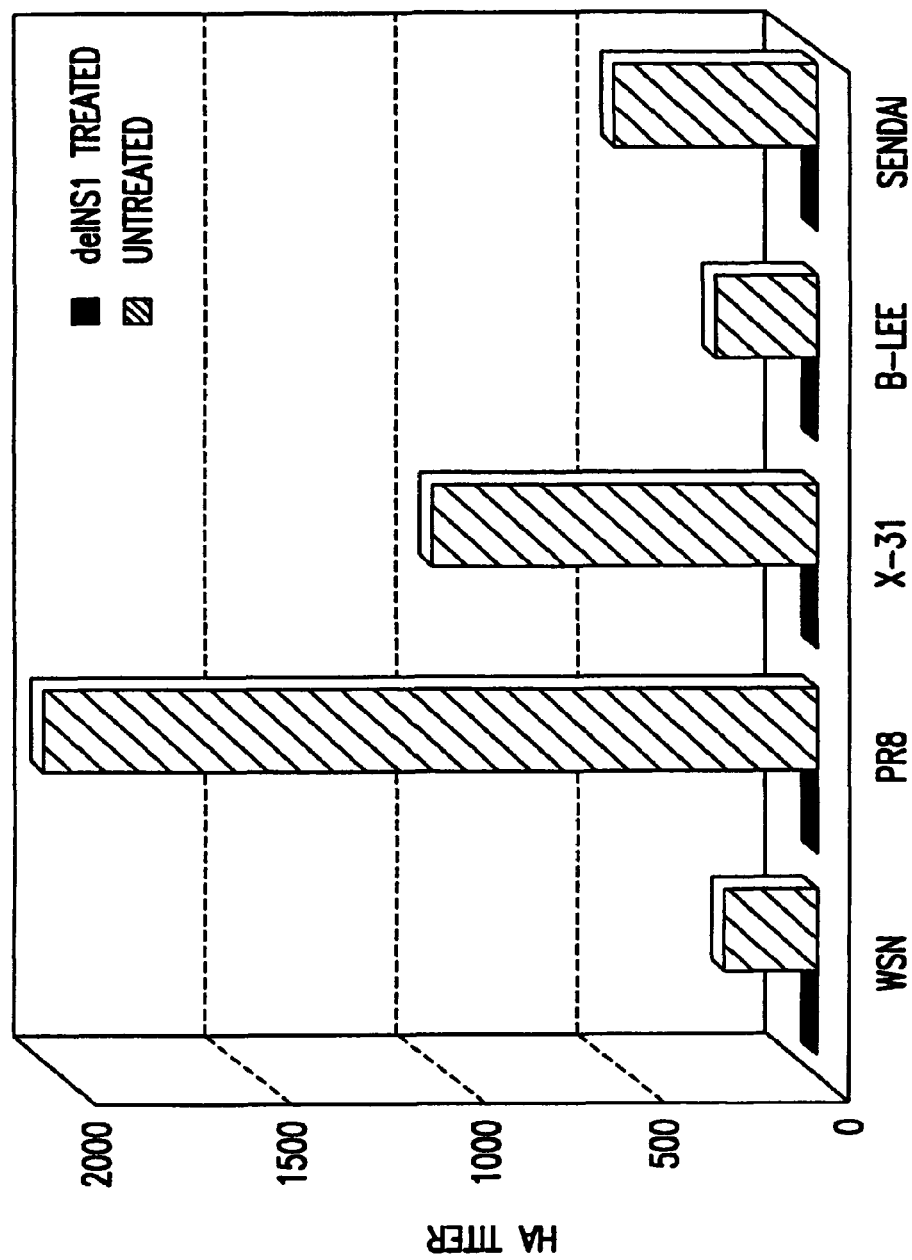

FIG. 2. Induction of an antiviral response in embryonated eggs by delNS1 virus. Ten-day-old embryonated chicken eggs were inoculated with PBS (untreated) or with $2 \times 10^4$ pfu of delNS1 virus (delNS1 treated). Eight hours later, the eggs were now infected with $10^3$ pfu of influenza A/WSN/33 (H1N1) virus, influenza A/PR8/34 (H+N1) virus, influenza A/X-31 (H3N2) virus, influenza B/Lee/40 virus, or Sendai virus. After two days of incubation, the allantoic fluid was harvested and virus titers were determined by a hemagglutination assay. Results are the average of two eggs.

Figure 3:
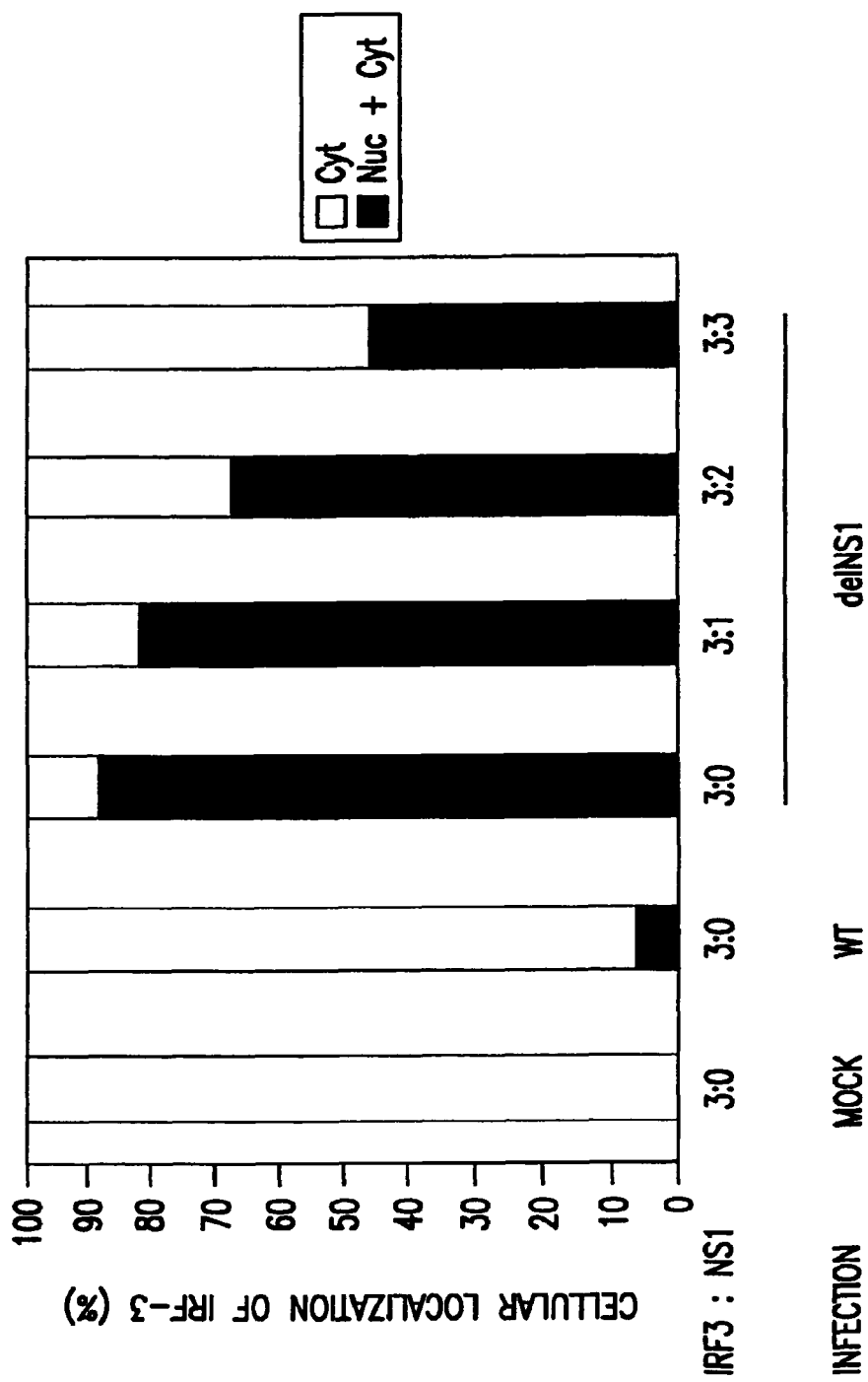

FIG. 3. CV1 cells were transfected with a plasmid expressing IRF-3 fused to the green fluorescent protein (GFP). This allowed determining the localization of IRF-3 inside the cells by fluorescence microscopy. In some cases, an NS1 expression plasmid was cotransfected with the IRF-3 expression plasmid at the indicated ratios. 24 hours posttransfection cells were infected at high moi with PR8 (WT) or with delNS1 virus as indicated. 10 hours postinfection, cells were analyzed in a fluorescence microscope for IRF-3-GFP localization. The percentage of cells showing exclusive cytoplasmic localization (CYT) and both cytoplasmic and nuclear localizations of IRF-3 (Nuc+Cyt) are indicated.

5. DETAILED DESCRIPTION OF THE INVENTION

The invention relates to the generation, selection and identification of attenuated negative strand RNA viruses that have an impaired ability to antagonize the cellular IFN response, and the use of such viruses in vaccine and pharmaceutical formulations.

The viruses can have segmented or non-segmented genomes and can be selected from naturally occurring strains, variants or mutants; mutagenized viruses (e.g., by exposure to UV irradiation, mutagens, and/or passaging); reassortants (for viruses with segmented genomes); and/or genetically engineered viruses. For example, the mutant viruses can be generated by natural variation, exposure to UV irradiation, exposure to chemical mutagens, by passaging in non-permissive hosts, by reassortment (i.e., by coinfection of an attenuated segmented virus with another strain having the desired antigens), and/or by genetic engineering (e.g., using "reverse genetics"). The viruses selected for use in the invention have defective IFN antagonist activity and are attenuated; i.e., they are infectious and can replicate in vivo, but only generate low titers resulting in subclinical levels of infection that are non-pathogenic. Such attenuated viruses are ideal candidates for live vaccines.

In a preferred embodiment, the attenuated viruses selected for use in the invention should be capable of inducing a robust IFN response in the host—a feature which contributes to the generation of a strong immune response when used as a vaccine, and which has other biological consequences that make the viruses useful as pharmaceutical agents for the prevention and/or treatment of other viral infections, or tumor formation in high risk individuals, or other diseases which are treated with IFN.

The invention is based, in part, on a number of discoveries and observations made by the Applicants when working with influenza virus mutants. However, the principles can be analogously applied and extrapolated to other segmented and non-segmented negative strand RNA viruses including, but not limited to paramyxoviruses (Sendai virus, parainfluenza virus, mumps, Newcastle disease virus), morbillivirus (measles virus, canine distemper virus and rinderpest virus); pneumovirus (respiratory syncytial virus and bovine respiratory virus); and rhabdovirus (vesicular stomatitis virus and lyssavirus).

First, the IFN response is important for containing viral infection in vivo. The Applicants found that growth of wild-type influenza virus A/WSN/33 in IFN-deficient mice (STAT1−/− mice) resulted in pan-organ infection; i.e., viral infection was not confined to the lungs as it is in wild-type mice which generate an IFN response (Garcia-Sastre, et al., 1998, J. Virol. 72:8550, which is incorporated by reference herein in its entirety). Second, the Applicants established that NS1 of influenza virus functions as an IFN antagonist. The Applicants discovered that an influenza virus mutant deleted of the entire NS1 gene (i.e., an NS1 "knockout") was not able to grow to high titers in IFN-competent host cells, and could only be propagated in IFN-deficient hosts. The NS1 knockout virus demonstrated an attenuated phenotype (i.e., it was lethal in IFN deficient STAT1−/− mice, but not in wild-type mice) and was found to be a potent inducer of IFN responses in host cells (Garcia-Sastre, et al., 1998, Virology 252:324-330, which is incorporated by reference herein in its entirety). Preinfection with the NS1 knockout mutant virus reduced titers of wild-type influenza and other viruses (e.g., Sendai) superinfected in embryonated eggs. In another experiment, infection with the NS1 knockout mutant influenza virus reduced foci formation in animals inoculated with tumor cells. Thus, the NS1 knockout influenza virus demonstrated interesting biological properties. However, the NS1 knockout mutant viruses could not be propagated in conventional systems for vaccine production. To overcome this problem, the Applicants used and developed IFN-deficient systems that allow for production of reasonable yields of attenuated virus.

In addition, the Applicants designed deletion mutants of NS1, which do not delete the entire gene. Surprisingly, these NS1 mutants were found to display an "intermediate" phenotype—the virus can be grown in conventional hosts used for propagating influenza virus (although growth is better in the IFN-deficient systems which yield higher titers). Most importantly, the deletion mutants are attenuated in vivo, and induce a robust IFN response. Vaccination with the influenza virus NS1 truncated mutants resulted in low titers of virus in animals subsequently challenged with wild-type virus, and afforded protection against disease.

The present invention also relates to the substrates designed for the isolation, identification and growth of viruses for vaccine purposes. In particular, interferon-deficient substrates for efficiently growing influenza virus mutants are described. In accordance with the present invention, an interferon-deficient substrate is one that is defective in its ability to produce or respond to interferon. The substrate of the present invention may be used for the growth of any number of viruses which may require interferon-deficient growth environment. Such viruses may include, but are not limited to paramyxoviruses (Sendai virus, parainfluenza virus, mumps, Newcastle disease virus), morbillivirus (measles virus, canine distemper virus and rinderpest virus); pneumovirus (respiratory syncytial virus and bovine respiratory virus); rhabdovirus (vesicular stomatitis virus and lyssavirus).

The invention also relates to the use of the attenuated virus of the invention in vaccines and pharmaceutical preparations for humans or animals. In particular, the attenuated viruses can be used as vaccines against a broad range of viruses and/or antigens, including but not limited to antigens of strain variants, different viruses or other infectious pathogens (e.g., bacteria, parasites, fungi), or tumor specific antigens. In another embodiment, the attenuated viruses, which inhibit viral replication and tumor formation, can be used for the prophylaxis or treatment of infection (viral or nonviral pathogens) or tumor formation or treatment of diseases for which IFN is of therapeutic benefit. Many methods may be used to introduce the live attenuated virus formulations to a human or animal subject to induce an immune or appropriate cytokine response. These include, but are not limited to, intranasal, intratrachial, oral, intradermal, intramuscular, intraperitoneal, intravenous and subcutaneous routes. In a preferred embodiment, the attenuated viruses of the present invention are formulated for delivery intranasally.

5.1 Generation of Mutants with Altered IFN Antagonist Activity

Any mutant virus or strain which has a decreased IFN antagonist activity can be selected and used in accordance with the invention. In one embodiment, naturally occurring mutants or variants, or spontaneous mutants can be selected that have an impaired ability to antagonize the cellular IFN response. In another embodiment, mutant viruses can be generated by exposing the virus to mutagens, such as ultraviolet irradiation or chemical mutagens, or by multiple passages and/or passage in non-permissive hosts. Screening in a differential growth system can be used to select for those mutants having impaired IFN antagonist function. For viruses with segmented genomes, the attenuated phenotype can be transferred to another strain having a desired antigen by reassortment, (i.e., by coinfection of the attenuated virus and the desired strain, and selection for reassortants displaying both phenotypes).

In another embodiment, mutations can be engineered into a negative strand RNA virus such as influenza, RSV, NDV, VSV and PIV, using "reverse genetics" approaches. In this way, natural or other mutations which confer the attenuated phenotype can be engineered into vaccine strains. For example, deletions, insertions or substitutions of the coding region of the gene responsible for IFN antagonist activity (such as the NS1 of influenza) can be engineered. Deletions, substitutions or insertions in the non-coding region of the gene responsible for IFN antagonist activity are also contemplated. To this end, mutations in the signals responsible for the transcription, replication, polyadenylation and/or packaging of the gene responsible or the IFN-antagonist activity can be engineered. For example, in influenza, such modifications can include but are not limited to: substitution of the non-coding regions of an influenza A virus gene by the non-coding regions of an influenza B virus gene (Muster, et al., 1991, Proc. Natl. Acad. Sci. USA, 88:5177), base pairs exchanges in the non-coding regions of an influenza virus gene (Fodor, et al., 1998, J. Virol. 72:6283), mutations in the promoter region of an influenza virus gene (Piccone, et al., 1993, Virus Res. 28:99; Li, et al., 1992, J. Virol. 66:4331), substitutions and deletions in the stretch of uridine residues at the 5' end of an influenza virus gene affecting polyadenylation (Luo, et al., 1991, J. Virol. 65:2861; Li, et al., J. Virol. 1994, 68(2):1245-9). Such mutations, for example to the promoter, could downregulate the expression of the gene responsible for IFN antagonist activity. Mutations in viral genes which may regulate the expression of the gene responsible for IFN antagonist activity are also within the scope of viruses that can be used in accordance with the invention.

The present invention also relates to mutations to the NS1 gene segment that may not result in an altered IFN antagonist activity or an IFN-inducing phenotype but rather results in altered viral functions and an attenuated phenotype e.g., altered inhibition of nuclear export of poly(A)-containing mRNA, altered inhibition of pre-mRNA splicing, altered inhibition of the activation of PKR by sequestering of dsRNA, altered effect on translation of viral RNA and altered inhibition of polyadenylation of host mRNA (e.g., see Krug in Textbook of Influenza, Nicholson et al. Ed. 1998, 82-92, and references cited therein).

The reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain. For example, antigens of non-related viruses such as HIV (gp160, gp120, gp41) parasite antigens (e.g., malaria), bacterial or fungal antigens or tumor antigens can be engineered into the attenuated strain. Alternatively, epitopes which alter the tropism of the virus in vivo can be engineered into the chimeric attenuated viruses of the invention.

In an alternate embodiment, a combination of reverse genetics techniques and reassortant techniques can be used to engineer attenuated viruses having the desired epitopes in segmented RNA viruses. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

In another embodiment, the virus to be mutated is a DNA virus (e.g., vaccinia, adenovirus, baculovirus) or a positive strand RNA virus (e.g., polio virus). In such cases, recombinant DNA techniques which are well known in the art may be used (e.g., see U.S. Pat. No. 4,769,330 to Paoletti, U.S. Pat. No. 4,215,051 to Smith each of which is incorporated herein by reference in its entirety).

Any virus may be engineered in accordance with the present invention, including but not limited to the families set forth in Table 2 below.

TABLE 2

FAMILIES OF HUMAN AND ANIMAL VIRUSES

| VIRUS CHARACTERISTICS | VIRUS FAMILY |
|---|---|
| dsDNA | |
| Enveloped | Poxviridae |
| | Irididoviridae |
| | Herpesviridae |
| Nonenveloped | Adenoviridae |
| | Papovaviridae |
| | Hepadnaviridae |

TABLE 2-continued

FAMILIES OF HUMAN AND ANIMAL VIRUSES

| VIRUS CHARACTERISTICS | VIRUS FAMILY |
| --- | --- |
| ssDNA | |
| Nonenveloped | Parvoviridae |
| dsRNA | |
| Nonenveloped | Reoviridae |
|  | Birnaviridae |
| ssRNA | |
| Enveloped | |
| Positive-Sense Genome | |
| No DNA Step in Replication | Togaviridae |
|  | Flaviviridae |
|  | Coronaviridae |
|  | Hepatitis C Virus |
| DNA Step in Replication | Retroviridae |
| Negative-Sense Genome | |
| Non-Segmented Genome | Paramyxoviridae |
|  | Rhabdoviridae |
|  | Filoviridae |
| Segmented Genome | Orthomyxoviridae |
|  | Bunyaviridae |
|  | Arenaviridae |
| Nonenveloped | Picornaviridae |
|  | Caliciviridae |

Abbreviations used: ds = double stranded; ss = single stranded; enveloped = possessing an outer lipid bilayer derived from the host cell membrane; positive-sense genome = for RNA viruses, genomes that are composed of nucleotide sequences that are directly translated on ribosomes, = for DNA viruses, genomes that are composed of nucleotide sequences that are the same as the mRNA; negative-sense genome = genomes that are composed of nucleotide sequences complementary to the positive-sense strand.

In a preferred embodiment, the present invention relates to genetically engineered influenza viruses containing deletions and/or truncations of the NS1 gene product. NS1 mutants of influenza A and B are particularly preferred. In one approach, portions of the amino terminal region of the NS1 gene product are retained whereas portions of the C-terminal region of the NS1 gene product are deleted. Specific desired mutations can be engineered by way of nucleic acid insertion, deletion, or mutation at the appropriate codon. In particular, the truncated NS1 proteins have from 1-60 amino acids, 1-70 amino acids, 1-80 amino acids, 1-90 amino acids (the N-terminal amino acid is 1), and preferably 90 amino acids; from 1-100 amino acids, and preferably 99 amino acids; from 1-110 amino acids; from 1-120 amino acids; or from 1-130 amino acids, and preferably 124 amino acids of the wildtype NS1 gene product.

The present invention also relates to any genetically engineered influenza virus in which the NS1 gene product has been modified by truncation or modification of the NS1 protein that confers upon the mutant viruses the following phenotypes: the ability of the viruses to grow to high titers in unconventional substrates, such as 6-7 day old chicken eggs, or the ability of the viruses to induce a host interferon response. For influenza A viruses, these include, but are not limited to: viruses having an NS1 truncations.

The present invention includes the use of naturally occurring mutant influenza viruses A or B having the attenuated phenotype, as well as influenza virus strains engineered to contain such mutations responsible for the attenuated phenotype. For influenza A viruses, these include, but are not limited to: viruses having an NS1 of 124 amino acids (Norton et al., 1987, Virology 156:204-213, which is incorporated by reference herein in its entirety). For influenza B viruses, these include, but are not limited to: viruses having an NS1 truncation mutant comprising 110 amino acids derived from the N-terminus (B/201) (Norton et al., 1987, Virology 156:204-213, which is incorporated by reference herein in its entirety), and viruses having an NS1 truncation mutant comprising 89 amino acids derived from the N-terminus (B/AWBY-234) (Tobita et al., 1990, Virology 174:314-19, which is incorporated by reference herein in its entirety). The present invention encompasses the use of naturally occurring mutants analogous to NS1/38, NS1/80, NS1/124, (Egorov, et al., 1998, J. Virol. 72(8):6437-41) as well as the naturally occurring mutants, A/Turkey/ORE/71, B/201 or B/AWBY-234. The present invention encompasses genetically engineering any influenza A or B virus such that the genome of the engineered virus comprises a mutation in the NS1 gene corresponding to the NS1 mutation found in naturally occurring mutants NS1/80, NS1/124, A/Turkey/ORE/71, B/201 or AWBY-234, with the proviso that the present invention does not comprise the following influenza mutants: A/Turkey/Ore/71, B/201 and AWBY-234 as they occur in nature.

The attenuated influenza virus may be further engineered to express antigens of other vaccine strains (e.g., using reverse genetics or reassortment). Alternatively, the attenuated influenza viruses may be engineered, using reverse genetics or reassortment with genetically engineered viruses, to express completely foreign epitopes, e.g., antigens of other infectious pathogens, tumor antigens, or targeting antigens. Since the NS RNA segment is the shortest among the eight viral RNAs, it is possible that the NS RNA will tolerate longer insertions of heterologous sequences than other viral genes. Moreover, the NS RNA segment directs the synthesis of high levels of protein in infected cells, suggesting that it would be an ideal segment for insertions of foreign antigens. However, in accordance with the present invention, any one of the eight segments of influenza viruses may be used for the insertion of heterologous sequences. For example, where surface antigen presentation is desired, segments encoding structural proteins, e.g., HA or NA may be used.

5.2 Host-Restriction Based Selection System

The invention encompasses methods of selecting viruses which have the desired phenotype, i.e., viruses which have low or no IFN antagonist activity, whether obtained from natural variants, spontaneous variants (i.e., variants which evolve during virus propagation), mutagenized natural variants, reassortants and/or genetically engineered viruses. Such viruses can be best screened in differential growth assays that compare growth in IFN-deficient versus IFN-competent host systems. Viruses which demonstrate better growth in the IFN-deficient systems versus IFN competent systems are selected; preferably, viruses which grow to titers at least one log greater in IFN-deficient systems as compared to an IFN-competent system are selected.

Alternatively, the viruses can be screened using IFN assay systems e.g., transcription based assay systems in which reporter gene expression is controlled by an IFN-responsive promoter. Reporter gene expression in infected versus uninfected cells can be measured to identify viruses which efficiently induce an IFN response, but which are unable to antagonize the IFN response. In a preferred embodiment, however, differential growth assays are used to select viruses having the desired phenotype, since the host system used (IFN-competent versus IFN-deficient) applies the appropriate selection pressure.

For example, growth of virus (as measured by titer) can be compared in a variety of cells, cell lines, or animal model systems that express IFN and the components of the IFN response, versus cells, cell lines, or animal model systems deficient for IFN or components of the IFN response. To this end, growth of virus in cell lines as VERO cells (which are IFN deficient) versus MDCK cells (which are IFN-competent) can be compared. Alternatively, IFN-deficient cell lines can be derived and established from animals bred or genetically engineered to be deficient in the INF system (e.g., STAT1−/− mutant mice). Growth of virus in such cell lines, as compared to IFN-competent cells derived, for example, from wild-type animals (e.g., wild-type mice) can be measured. In yet another embodiment, cell lines which are IFN-competent and known to support the growth of wild type virus can be engineered to be IFN-deficient, (e.g., by knocking out STAT1, IRF3, PKR, etc.) Techniques which are well known in the art for the propagation of viruses in cell lines can be used (see, for example, the working examples infra). Growth of virus in the standard IFN competent cell line versus the IFN deficient genetically engineered cell line can be compared.

Animal systems can also be used. For example, for influenza, growth in young, IFN-deficient embryonated eggs, e.g., about 6 to about 8 days old, can be compared to growth in older, IFN-competent eggs, e.g., about 10 to 12 days old. To this end, techniques well known in the art for infection and propagation in eggs can be used (e.g., see working examples, infra). Alternatively, growth in IFN-deficient STAT1−/− mice can be compared to IFN-competent wild type mice. In yet another alternative, growth in IFN-deficient embryonated eggs produced by, for example, STAT1−/− transgenic fowl can be compared to growth in IFN-competent eggs produced by wild-type fowl.

For purposes of screening, however, transient IFN-deficient systems can be used in lieu of genetically manipulated systems. For example, the host system can be treated with compounds that inhibit IFN production and/or components of the IFN response (e.g., drugs, antibodies against IFN, antibodies against IFN-receptor, inhibitors of PKR, antisense molecules and ribozymes, etc.). Growth of virus can be compared in IFN-competent untreated controls versus IFN-deficient treated systems. For example, older eggs which are IFN-competent can be pretreated with such drugs prior to infection with the virus to be screened. Growth is compared to that achieved in untreated control eggs of the same age.

The screening methods of the invention provide a simple and easy screen to identify mutant viruses with abolished IFN antagonist activity by the inability of the mutant virus to grow in IFN-responsive environments, as compared to the ability of the mutant virus to grow in IFN-deficient environments. The screening methods of the invention may also be used to identify mutant viruses with altered, but not abolished IFN antagonist activity by measuring the ability of the mutant virus to grow in both IFN-responsive e.g., 10-day old embryonated eggs or MDCK cells and IFN-deficient environments e.g., 6-to-7-day old embryonated eggs or Vero cells. For example, influenza viruses showing at least one log lower titers in 10-days-old eggs versus 6-7 days old eggs will be considered impaired in their ability to inhibit the IFN response. In another example, influenza viruses showing at least one log lower titer in 12 day old eggs (which mount a high IFN response) versus 10 day old eggs (which mount a moderate IFN response) are considered partially impaired in their ability to antagonize the IFN response, and are considered attractive vaccine candidates.

The selection methods of the invention also encompass identifying those mutant viruses which induce IFN responses. In accordance with the selection methods of the invention, induction of IFN responses may be measured by assaying levels of IFN expression or expression of target genes or reporter genes induced by IFN following infection with the mutant virus or activation of transactivators involved in the IFN expression and/or the IFN response.

In yet another embodiment of the selection systems of the invention, induction of IFN responses may be determined by measuring the phosphorylated state of components of the IFN pathway following infection with the test mutant virus, e.g., IRF-3, which is phosphorylated in response to double-stranded RNA. In response to type I IFN, Jak1 kinase and TyK2 kinase, subunits of the IFN receptor, STAT1, and STAT2 are rapidly tyrosine phosphorylated. Thus, in order to determine whether the mutant virus induces IFN responses, cells, such as 293 cells, are infected with the test mutant virus and following infection, the cells are lysed. IFN pathway components, such as Jak1 kinase or TyK2 kinase, are immunoprecipitated from the infected cell lysates, using specific polyclonal sera or antibodies, and the tyrosine phosphorylated state of the kinase is determined by immunoblot assays with an anti-phosphotyrosine antibody (e.g., see Krishnan et al. 1997, Eur. J. Biochem. 247: 298-305). An enhanced phosphorylated state of any of the components of the IFN pathway following infection with the mutant virus would indicate induction of IFN responses by the mutant virus.

In yet another embodiment, the selection systems of the invention encompass measuring the ability to bind specific DNA sequences or the translocation of transcription factors induced in response to viral infection, e.g., IRF3, STAT1, STAT2, etc. In particular, STAT1 and STAT2 are phosphorylated and translocated from the cytoplasm to the nucleus in response to type I IFN. The ability to bind specific DNA sequences or the translocation of transcription factors can be measured by techniques known to those of skill in the art, e.g., electromobility gel shift assays, cell staining, etc.

In yet another embodiment of the selection systems of the invention, induction of IFN responses may be determined by measuring IFN-dependent transcriptional activation following infection with the test mutant virus. In this embodiment, the expression of genes known to be induced by IFN, e.g., Mx, PKR, 2-5-oligoadenylatesynthetase, major histocompatibility complex (MHC) class I, etc., can be analyzed by techniques known to those of skill in the art (e.g., northern blots, western blots, PCR, etc.). Alternatively, test cells such as human embryonic kidney cells or human osteogenic sarcoma cells, are engineered to transiently or constitutively express reporter genes such as luciferase reporter gene or chloramphenicol transferase (CAT) reporter gene under the control of an interferon stimulated response element, such as the IFN-stimulated promoter of the ISG-54K gene (Bluyssen et al., 1994, Eur. J. Biochem. 220:395-402). Cells are infected with the test mutant virus and the level of expression of the reporter gene compared to that in uninfected cells or cells infected with wild-type virus. An increase in the level of expression of the reporter gene following infection with the test virus would indicate that the test mutant virus is inducing an IFN response.

In yet another embodiment, the selection systems of the invention encompass measuring IFN induction by determining whether an extract from the cell or egg infected with the test mutant virus is capable of conferring protective activity against viral infection. More specifically, groups of 10-day old embryonated chicken eggs are infected with the test mutant virus or the wild-type virus. Approximately 15 to 20 hours post infection, the allantoic fluid is harvested and tested for IFN activity by determining the highest dilution with protective activity against VSV infection in tissue culture cells, such as CEF cells.

5.3 Propagation of Virus in Interferon Deficient Growth Substrates

The invention also encompasses methods and IFN-deficient substrates for the growth and isolation of naturally occurring or engineered mutant viruses having altered IFN antagonist activity. IFN-deficient substrates which can be used to support the growth of the attenuated mutant viruses include, but are not limited to naturally occurring cells, cell lines, animals or embryonated eggs that are IFN deficient, e.g., Vero cells, young embryonated eggs; recombinant cells or cell lines that are engineered to be IFN deficient, e.g., IFN-deficient cell lines derived from STAT1 knockout mice or other similarly engineered transgenic animals; embryonated eggs obtained from IFN deficient birds, especially fowl (e.g., chickens, ducks, turkeys) including flock that are bred to be IFN-deficient or transgenic birds (e.g., STAT1 knockouts). Alternatively, the host system, cells, cell lines, eggs or animals can be genetically engineered to express transgenes encoding inhibitors of the IFN system, e.g., dominant-negative mutants, such as STAT1 lacking the DNA binding domain, antisense RNA, ribozymes, inhibitors of IFN production, inhibitors of IFN signaling, and/or inhibitors of antiviral genes induced by IFN. It should be recognized that animals that are bred or genetically engineered to be IFN deficient will be somewhat immunocompromised, and should be maintained in a controlled, disease free environment. Thus, appropriate measures (including the use of dietary antibiotics) should be taken to limit the risk of exposure to infectious agents of transgenic IFN deficient animals, such as flocks of breeding hens, ducks, turkeys, etc. Alternatively, the host system, e.g., cells, cell lines, eggs or animals can be treated with a compound which inhibits IFN production and/or the IFN pathway e.g., drugs, antibodies, antisense molecules, ribozyme molecules targeting the STAT1 gene, and/or antiviral genes induced by IFN.

In accordance with the present invention, immature embryonated chicken eggs encompass eggs which as a course of nature are up to, but not yet ten-day-old eggs, preferably six-to nine-day-old eggs; and eggs which artificially mimic immature eggs up to, but not yet ten-day-old, as a result of alterations to the growth conditions, e.g., changes in incubation temperatures; treating with drugs; or any other alteration which results in an egg with a retarded development, such that the IFN system of the egg is not fully developed as compared to 10- to 12-day-old eggs.

5.3.1 Natural IFN Deficient Substrates

In one embodiment, the present invention relates to growing naturally occurring and engineered mutant viruses in unconventional substrates, such as immature embryonated eggs which have not yet developed an IFN system. Immature embryonated eggs are normally not used to grow virus due to their fragile condition and smaller allantoic volume. The present invention encompasses growing mutant viruses in embryonated eggs less than 10 days old; preferably growing mutated virus in 8-day old embryonated eggs and most preferably, in 6 to 8-day old eggs.

The present invention also encompasses methods of growing and isolating mutated viruses having altered IFN antagonist activity in cells and cell lines which naturally do not have an IFN pathway or have a deficient IFN pathway or have a deficiency in the IFN system e.g., low levels of IFN expression as compared to wild-type cells. In a particular preferred embodiment, the present invention relates to methods of growing mutated viruses having an altered IFN antagonist activity in Vero cells.

5.3.2 Genetically Engineered IFN Deficient Substrates

The present invention relates to methods of growing and isolating mutated viruses having altered IFN antagonist activity in a genetically engineered IFN deficient substrate. The present invention encompasses transgenic avians in which a gene essential to the IFN system is mutated, e.g., STAT1, which would lay eggs that are IFN deficient. The present invention further encompasses avian transgenics which express dominant-negative transcription factors, e.g., STAT1 lacking the DNA binding domain, ribozymes, antisense RNA, inhibitors of IFN production, inhibitors of IFN signaling, and inhibitors of antiviral genes induced in response to IFN. The benefit of using eggs from an IFN-deficient transgenic avian is that the conventional 10 day age eggs may be used to grow the virus which are more stable and have a larger volume due to their larger size. In yet another embodiment, cell lines may be genetically engineered to be IFN deficient. The present invention encompasses cell lines in which a gene essential to the IFN synthesis, IFN pathway, and/or an antiviral gene(s) induced by IFN are mutated, e.g., STAT1.

The invention provides recombinant cell lines or animals, in particular avians, in which one or more genes essential for the IFN pathway, e.g. interferon receptor, STAT1 etc. has been disrupted, i.e., is a "knockout"; the recombinant animal can be any animal but in a preferred embodiment is an avian, e.g. chicken, turkey, hen, duck, etc. (see, e.g., Sang, 1994, Trends Biotechnol. 12:415; Perry, et al., 1993, Transgenic Res. 2:125; Stern, C. D., 1996, Curr Top Microbiol Immunol 212:195-206; and Shuman, 1991, Experientia 47:897 for reviews regarding the production of avian transgenics each of which is incorporated by reference herein in its entirety). Such a cell line or animal can be generated by any method known in the art for disrupting a gene on the chromosome of the cell or animal. Such techniques include, but are not limited to pronuclear microinjection (Hoppe & Wagner, 1989, U.S. Pat. No. 4,873,191); retrovirus mediated gene transfer into germ lines (Van der Putten et al., 1985, Proc. Natl. Acad. Sci., USA 82:6148-6152); gene targeting in embryonic stem cells (Thompson et al., 1989, Cell 56:313); electroporation of embryos (Lo, 1983, Mol. Cell. Biol. 3:1803); and sperm-mediated gene transfer (Lavitrano et al., 1989, Cell 57:717); etc. For a review of such techniques, see Gordon, 1989, Transgenic Animals, Intl. Rev. Cytol. 115:171, which is incorporated by reference herein in its entirety.

In particular, a STAT1 knockout animal can be produced by promoting homologous recombination between a STAT1 gene in its chromosome and an exogenous STAT1 gene that has been rendered biologically inactive (preferably by insertion of a heterologous sequence, e.g., an antibiotic resistance gene). Homologous recombination methods for disrupting genes in the mouse genome are described, for example, in Capecchi (1989, Science 244:1288) and Mansour et al. (1988, Nature 336:348).

Briefly, all or a portion of a STAT1 genomic clone is isolated from genomic DNA from the same species as the knockout cell or animal. The STAT1 genomic clone can be isolated by any method known in the art for isolation of genomic clones (e.g. by probing a genomic library with a probe derived from a STAT1 sequence such as those sequences provided in see Meraz et al., 1996, Cell 84:431; Durbin et al. 1996, Cell 84:443, and references cited therein). Once the genomic clone is isolated, all or a portion of the clone is introduced into a recombinant vector. Preferably, the portion of the clone introduced into the vector contains at least a portion of an exon of the STAT1 gene, i.e., contains a STAT1 protein coding sequence. A sequence not homologous to the STAT1 sequence, preferably a positive selectable marker, such as a gene encoding an antibiotic resistance gene, is then introduced into the STAT1 gene exon. The selectable marker is preferably operably linked to a promoter, more preferably a constitutive promoter. The non-homologous sequence is introduced anywhere in the STAT1 coding sequence that will disrupt STAT1 activity, e.g., at a position where point mutations or other mutations have been demonstrated to inactivate STAT1 protein function. For example, but not by way of limitation, the non-homologous sequence can be inserted into the coding sequence for the portion of the STAT1 protein containing all or a portion of the kinase domain (e.g., the nucleotide sequence coding for at least 50, 100, 150, 200 or 250 amino acids of the kinase domain).

The positive selectable marker is preferably a neomycin resistance gene (neo gene) or a hygromycin resistance gene (hygro gene). The promoter may be any promoter known in the art; by way of example the promoter may be the phosphoglycerate kinase (PGK) promoter (Adra et al., 1987, Gene 60:65-74), the PolII promoter (Soriano et al., 1991. Cell 64:693-701), or the MC1 promoter, which is a synthetic promoter designed for expression in embryo-derived stem cells (Thomas & Capecchi, 1987, Cell 51:503-512). Use of a selectable marker, such as an antibiotic resistance gene, allows for the selection of cells that have incorporated the targeting vector (for example, the expression of the neo gene product confers resistance to G418, and expression of the hygro gene product confers resistance to hygromycin).

In a preferred embodiment, a negative selectable marker for a counterselection step for homologous, as opposed to non-homologous, recombination of the vector is inserted outside of the STAT1 genomic clone insert. For example, such a negative selectable marker is the HSV thymidine kinase gene (HSV-tk), the expression of which makes cells sensitive to ganciclovir. The negative selectable marker is preferably under the control of a promoter such as, but not limited to the PGK promoter, the PolII promoter or the MC1 promoter.

When homologous recombination occurs, the portions of the vector that are homologous to the STAT1 gene, as well as the non-homologous insert within the STAT1 gene sequences, are incorporated into the STAT1 gene in the chromosome, and the remainder of the vector is lost. Thus, since the negative selectable marker is outside the region of homology with the STAT1 gene, cells in which homologous recombination has occurred (or their progeny), will not contain the negative selectable marker. For example, if the negative selectable marker is the HSV-tk gene, the cells in which homologous recombination has occurred will not express thymidine kinase and will survive exposure to ganciclovir. This procedure permits the selection of cells in which homologous recombination has occurred, as compared to non-homologous recombination in which it is likely that the negative selectable marker is also incorporated into the genome along with the STAT1 sequences and the positive selectable marker. Thus, cells in which non-homologous recombination has occurred would most likely express thymidine kinase and be sensitive to ganciclovir.

Once the targeting vector is prepared, it is linearized with a restriction enzyme for which there is a unique site in the targeting vector, and the linearized vector is introduced into embryo-derived stem (ES) cells (Gossler et al., 1986, Proc. Natl. Acad. Sci. USA 83:9065-9069) by any method known in the art, for example by electroporation. If the targeting vector includes a positive selectable marker and a negative, counterselectable marker, the ES cells in which homologous recombination has occurred can be selected by incubation in selective media. For example, if the selectable markers are the neo resistance gene and the HSV-tk gene, the cells are exposed to G418 (e.g., approximately 300 μg/ml) and ganciclovir (e.g., approximately 2 μM).

Any technique known in the art for genotyping, for example but not limited to Southern blot analysis or the polymerase chain reaction, can be used to confirm that the disrupted STAT1 sequences have homologously recombined into the STAT1 gene in the genome of the ES cells. Because the restriction map of the STAT1 genomic clone is known and the sequence of the STAT1 coding sequence is known (see Meraz et al., 1996, Cell 84:431; Durbin et al., 1996, Cell 84: 443-450, all references cited therein), the size of a particular restriction fragment or a PCR amplification product generated from DNA from both the disrupted and non-disrupted alleles can be determined. Thus, by assaying for a restriction fragment or PCR product, the size of which differs between the disrupted and non-disrupted STAT1 gene, one can determine whether homologous recombination has occurred to disrupt the STAT1 gene.

The ES cells with the disrupted STAT1 locus can then be introduced into blastocysts by microinjection and then the blastocysts can be implanted into the uteri of pseudopregnant mice using routine techniques. The animal that develop from the implanted blastocysts are chimeric for the disrupted allele. The chimeric males can be crossed to females, and this cross can be designed such that germline transmission of the allele is linked to transmission of a certain coat color. The germline transmission of the allele can be confirmed by Southern blotting or PCR analysis, as described above, of genomic DNA isolated from tissue samples.

5.3.3 Transient IFN Deficient Substrates

The cells, cell lines, animals or eggs can be pretreated with compounds that inhibit the IFN system. In accordance with the present invention, compounds which inhibit synthesis of IFN, or the activity or the expression of the components of the IFN system can be used to pretreat hosts, e.g., compounds that inhibit the synthesis of IFN, the activity of IFN, the IFN receptor, other targets in the IFN signal transduction pathway, or that inhibit the activity of antiviral genes induced by IFN. Examples of compounds which may be used in accordance with the present invention, include, but are not limited to, nucleic acid molecules, antibodies, peptides, antagonists of the IFN receptor, inhibitors of the STAT1 pathway, inhibitors of PKR, etc. In accordance with the present invention, nucleic acid molecules include antisense molecules, ribozymes and triple helix molecules that target genes encoding essential components of the IFN system, e.g., STAT1. Nucleic acid molecules also encompass nucleotides encoding dominant negative mutants of components of the IFN system; e.g. prior to infection with the viral mutant, the cells can be transfected with a DNA encoding a truncated, signalling incompetent mutant of the IFN receptor.

Dominant-negative mutants which may be used in accordance with the present invention to inhibit the IFN pathway include kinase deficient versions of Jak1, TyK2 or transcription factors lacking DNA binding domains STAT1, and STAT2 (see, e.g., Krishnan et al., 1997, Eur. J. Biochem. 247: 298-305)

5.4 Vaccine Formulations

The invention encompasses vaccine formulations comprising the attenuated negative strand RNA viruses having an impaired ability to antagonize the cellular IFN response, and a suitable excipient. The virus used in the vaccine formulation may be selected from naturally occurring mutants or variants, mutagenized viruses or genetically engineered viruses. Attenuated strains of segmented RNA viruses can also be generated via reassortment techniques, or by using a combination of the reverse genetics approach and reassortment techniques. Naturally occurring variants include viruses isolated from nature as well as spontaneous occurring variants generated during virus propagation, having an impaired ability to antagonize the cellular IFN response. The attenuated virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Vaccine formulations may include genetically engineered negative strand RNA viruses that have mutations in the NS1 or analogous gene including but not limited to the truncated NS1 influenza mutants described in the working examples, infra. They may also be formulated using natural variants, such as the A/turkey/Ore/71 natural variant of influenza A, or B/201, and B/AWBY-234, which are natural variants of influenza B. When formulated as a live virus vaccine, a range of about $10^4$ pfu to about $5 \times 10^6$ pfu per dose should be used.

Many methods may be used to introduce the vaccine formulations described above, these include but are not limited to intranasal, intratracheal, oral, intradermal, intramuscular, intraperitoneal, intravenous, and subcutaneous routes. It may be preferable to introduce the virus vaccine formulation via the natural route of infection of the pathogen for which the vaccine is designed, or via the natural route of infection of the parental attenuated virus. Where a live influenza virus vaccine preparation is used, it may be preferable to introduce the formulation via the natural route of infection for influenza virus. The ability of influenza virus to induce a vigorous secretory and cellular immune response can be used advantageously. For example, infection of the respiratory tract by influenza viruses may induce a strong secretory immune response, for example in the urogenital system, with concomitant protection against a particular disease causing agent.

A vaccine of the present invention, comprising $10^4$-$5 \times 10^6$ pfu of mutant viruses with altered IFN antagonist activity, could be administered once. Alternatively, a vaccine of the present invention, comprising $10^4$-$5 \times 10^6$ pfu of mutant viruses with altered IFN antagonist activity, could be administered twice or three times with an interval of 2 to 6 months between doses. Alternatively, a vaccine of the present invention, comprising $10^4$-$5 \times 10^6$ pfu of mutant viruses with altered IFN antagonist activity, could be administered as often as needed to an animal, preferably a mammal, and more preferably a human being.

5.5 Pharmaceutical Compositions

The present invention encompasses pharmaceutical compositions comprising mutant viruses with altered IFN antagonist activity to be used as anti-viral agents or antitumor agents or as agents against IFN-sensitive diseases. The pharmaceutical compositions have utility as an anti-viral prophylactic and may be administered to an individual at risk of getting infected or is expected to be exposed to a virus. For example, in the event that a child comes home from school where he is exposed to several classmates with the flu, a parent would administer the anti-viral pharmaceutical composition of the invention to herself, the child and other family members to prevent viral infection and subsequent illness. People traveling to parts of the world where a certain infectious disease is prevalent (e.g. hepatitis A virus, malaria, etc.) can also be treated.

Alternatively, the pharmaceutical compositions may be used to treat tumors or prevent tumor formation, e.g., in patients who have cancer or in those who are at high risk for developing neoplasms or cancer. For example, patients with cancer can be treated to prevent further tumorigenesis. Alternatively, subjects who are or are expected to be exposed to carcinogens can be treated; individuals involved in environmental cleanups who may be exposed to pollutants (e.g. asbestos) may be treated. Alternatively, individuals who are to be exposed to radiation can be treated prior to exposure and thereafter (e.g. patients exposed to high dose radiation or who must take carcinogenic drugs).

The use of the attenuated viruses of the invention as anti-tumor agents is based on the Applicants' discovery that an attenuated influenza virus mutant containing a deletion in its IFN-antagonist gene is able to reduce tumor formation in mice. The antitumor properties of the invention can be at least partially related to their ability to induce IFN and IFN responses. Alternatively, the antitumor properties of the attenuated viruses of the invention can be related to their ability to specifically grow in and kill tumor cells, many of which are known to have deficiencies in the IFN system. Regardless of the molecular mechanism(s) responsible for the antitumor properties, the attenuated viruses of the invention might be used to treat tumors or to prevent tumor formation.

The present invention further encompasses the mutant viruses with an altered IFN-antagonist phenotype which are targeted to specific organs, tissues and/or cells in the body in order to induce therapeutic or prophylactic effects locally. One advantage of such an approach is that the IFN-inducing viruses of the invention are targeted to specific sites, e.g. the location of a tumor, to induce IFN in a site specific manner for a therapeutic effect rather than inducing IFN systemically which may have toxic effects.

The mutant IFN-inducing viruses of the invention may be engineered using the methods described herein to express proteins or peptides which would target the viruses to a particular site. In a preferred embodiment, the IFN-inducing viruses would be targeted to sites of tumors. In such an embodiment, the mutant viruses can be engineered to express the antigen combining site of an antibody which recognized the tumor specific antigen, thus targeting the IFN-inducing virus to the tumor. In yet another embodiment, where the tumor to be targeted expresses a hormone receptor, such as breast or ovarian tumors which express estrogen receptors, the IFN-inducing virus may be engineered to express the appropriate hormone. In yet another embodiment, where the tumor to be targeted expresses a receptor to a growth factor, e.g., VEGF, EGF, or PDGF, the IFN-inducing virus may be engineered to express the appropriate growth factor or portion(s) thereof. Thus, in accordance with the invention, the IFN-inducing viruses may be engineered to express any target gene product, including peptides, proteins, such as enzymes, hormones, growth factors, antigens or antibodies, which will function to target the virus to a site in need of anti-viral, antibacterial, anti-microbial or anti-cancer activity.

Methods of introduction include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249: 1527-1533).

The pharmaceutical compositions of the present invention comprise a therapeutically effective amount of the attenuated virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for administration are generally about $10^4$-$5 \times 10^6$ pfu and can be administered once, or multiple times with intervals as often as needed. Pharmaceutical compositions of the present invention comprising $10^4$-$5 \times 10^6$ pfu of mutant viruses with altered IFN antagonist activity, can be administered intranasally, intratracheally, intramuscularly or subcutaneously. Effective doses may be extrapolated from dose-response curves derived from in vitro or animal model test systems.

6. EXAMPLE

Generation and Characterization of NS1 Truncation Mutants of Influenza A Virus 6.1 Materials and Methods Influenza A/PR/8/34 (PR8) virus was propagated in 10-day-old embryonated chicken eggs at 37° C. Influenza A virus 25A-1, a reassortant virus containing the NS segment from the cold-adapted strain A/Leningrad/134/47/57 and the remaining genes from PR8 virus (Egorov et al., 1994, Vopr. Virusol. 39:201-205; Shaw et al., 1996, in Options of the control of influenza III, eds. Brown, Hampson Webster (Elsevier Science) pp. 433-436) was grown in Vero cells at 34° C. The 25A-1 virus is temperature sensitive in mammalian cells, and was used as a helper virus for the rescue of the NS1/99 transfectant virus. Vero cells and MDCK cells maintained in minimal essential medium (MEM) containing 1 µg/ml of trypsin (Difco Laboratories, Detroit, Mich.) were used for influenza virus growth. Vero cells were also used for selection, plaque purification and titration of the NS1/99 virus. MDCK cells were maintained in DMEM (Dulbecco's minimal essential medium) containing 10% heat-inactivated fetal calf serum. Vero cells were grown in AIM-V medium (Life Technologies, Grand Island, N.Y.).

The plasmid pT3NS1/99, which contains a 99 amino acid C-terminal truncated form of NS1 was made as follows. First, pPUC19-T3/NS PR8, containing the complete NS gene of PR8 virus flanked by the T3 RNA polymerase promoter and BpuAI restriction site was amplified by reverse PCR (Ochman et al., 1988, Genetics 120:621-623) using the appropriate primers. The obtained cDNA thus containing the truncated NS1 gene was phosphorylated, Klenow treated, self-ligated and propagated in E. coli strain TG1. The construct obtained after purification was named pT3NS1/99 and verified by sequencing. Plasmids for expression of NP, PB1, PB2, and PA proteins of PR8 virus (pHMG-NP, pHMG-PB1, pHMG-PB2, and pHMG-PA) were previously described (Pleschka et al., 1996, J. Virol. 70:4188-4192). pPOLI-NS-RB was made by substituting the CAT open reading frame of pPOLI-CAT-RT (Pleschka et al., 1996, J. Virol. 70:4188-4192) within RT-PCR product derived from the coding region of the NS gene of influenza A/WSN/33 (WSN) virus. This plasmid expresses the NS-specific viral RNA segment of WSN virus under the control of a truncated human polymerase I promoter.

Generation of NS1/99 virus was performed by ribonucleoprotein (RNP) transfection (Luytjes et al., 1989, Cell 59:1107-1113). The RNPs were formed by T3 RNA polymerase transcription from pT3NS1/99 linearized with BpuAI in the presence of purified nucleoprotein and polymerase of influenza 25A-1 virus (Enami, et al., 1991, J. Virol. 65:2711-2713). RNP complexes were transfected into Vero cells which were previously infected with 25A-1 virus. Transfected cells were incubated for 18 hours at 37° C., and the supernatant was passaged twice in Vero cells at 40° C. and plaque purified three times in Vero cells covered with agar overlay media at 37° C. The isolated NS1/99 virus was analyzed by RT-PCR using specific primers. The wild-type transfectant virus was generated as follows: Vero cells in 35-mm dishes were transfected with plasmids pHMG-NP, pHMG-PB1, pHMG-PB2, pHMG-PA and pPOLI-NS-RB, as previously described (Pleschka et al., 1996, J. Virol. 70:4188-4192). Two days post-transfection, cells were infected with $5 \times 10^4$ pfu of delNS1 virus and incubated two more days at 37° C. Cell supernatant was passaged once in MDCK cells and twice in chicken embryonated eggs. Transfectant viruses were cloned by limiting dilution in eggs. Genomic RNA from purified NS1/99 transfectant virus was analyzed by polyacrylamide gel electrophoresis, as previously described (Zheng et al., 1996, Virology 217:242-251). Expression of a truncated NS1 protein by NS1/99 virus was verified by immunoprecipitating labeled infected cell extracts using a rabbit polyclonal antisera against NS1.

The allantoic cavity of embryonated chicken eggs, aged 6, 10, and 14 days were inoculated with approximate $10^3$ pfu of PR8, NS1/99, or delNS1 (in which the entire NS1 gene is deleted) viruses, incubated at 37° C. for two days, and the viruses present in the allantoic fluid were titrated by hemagglutination (HA) assay.

Groups of 5 BALB/c mice (Taconic Farms) were inoculated intranasally with $5 \times 10^6$ pfu, $1.5 \times 10^5$ pfu, or $5 \times 10^3$ pfu of wild-type A/PR/8/34 (PR8) or NS1/99 virus. Inoculations were performed under anesthesia using 50 µl of MEM containing the appropriate number of plaque forming units of the appropriate virus. Animals were monitored daily, and sacrificed when observed in extremis. In a subsequent experiment, all surviving mice were challenged four weeks later with a dose of $100 LD_{50}$ of wild-type PR8 virus. All procedures were in accord with NIH guidelines on care and use of laboratory animals.

6.2 Results

Attenuation of Influenza A Viruses by NS1 Deletions

Applicants have previously shown that an influenza A virus in which the NS1 gene was deleted (delNS1 virus) is able to grow to titers of approximately $10^7$ pfu/ml in cells deficient in type I Interferon (IFN) production, such as Vero cells. However, this virus was impaired in its ability to replicate and cause disease in mice (Garcia-Sastre et al., 1998, Virology 252:324). By contrast, delNS1 virus was able to grow in and kill STAT1–/– mice. These results demonstrated that the NS1 protein of influenza A virus is a virulence factor involved in the inhibition of the host antiviral responses mediated by type I IFN. The following experiments were conducted to determine whether one could generate influenza viruses with virulence characteristics intermediate between wild-type and delNS1 viruses by deleting portions of the NS1 gene and whether some of these viruses might have optimal characteristics for being used as live attenuated vaccines against influenza viruses, i.e., stability and an appropriate balance between attenuation, immunogenicity and growth in substrates suitable for vaccine preparation, such as embryonated chicken eggs.

In order to test this hypothesis, an influenza A/PR/8/34 (PR8) virus was generated in which the NS1 gene has been modified in order to direct the expression of a truncated NS1 protein containing only 99 amino acids at the amino terminal in common with the 230 amino acids of the wild-type NS1 protein. This virus (NS1-99) was obtained by RNP transfection of an artificially engineered NS gene using 25A-1 helper virus, as previously described (Garcia-Sastre et al., 1998, Virology 252:324). Analysis of NS1 expression in virus infected cells revealed the truncated nature of the NS1 protein of the NS1-99 virus.

The ability of delNS1, NS1-99 and wild-type PR8 viruses to grow in embryonated chicken eggs of different ages was analyzed. The rationale for this experiment comes from the fact that the ability of embryonated eggs to synthesize and to respond to type I IFN under an appropriate stimulus is age dependent. In fact, both IFN inducibility and responsiveness start at an age of approximately 10 days, and then exponentially increase with the age (Sekellick et al. 1990, In Vitro Cell. Dev. Biol. 26:997; Sekellick & Marcus, 1985 J. Interferon Res. 5:657). Thus, the use of eggs of different ages represents a unique system to test the ability of different viruses to inhibit IFN responses. Eggs of 6, 10, and 14 days of age were inoculated with approximately $10^3$ pfu of PR8, NS1-99 or delNS1 viruses, incubated at 37° C. for 2 days, and the viruses present in the allantoic fluid were titrated by hemagglutination (HA) assay. As shown in Table 3, whereas wild-type virus grew to similar HA titers in embryonated eggs of 6, 10 and 14 days of age, delNS1 only replicated to a detectable HA titer in 6-day-old eggs. By contrast, NS1-99 virus showed an intermediate behavior between delNS1 and wild-type viruses, and was able to grow to HA titers similar to those of wild-type virus in 10-day-old eggs, but not in 14-day-old eggs.

TABLE 3

Virus replication in embryonated chicken eggs.

| | Hemagglutination titer[1] Age of eggs: | | |
|---|---|---|---|
| Virus | 6 days | 10 days | 14 days |
| WT PR8[2] | 2,048 | 4,096 | 1,071 |
| NS1/99 | N.D.[3] | 2,048 | <2 |
| delNS1 | 64 | <2 | <2 |

[1]Titers represent the highest dilution with hemagglutinating activity.
[2]Wild-type influenza A/PR/8/34 virus.
[3]Not determined.

The attenuation characteristics of NS1-99 virus were next determined in mice. For this purpose, groups of 5 BALB/c mice were intranasally infected with $5 \times 10^6$ pfu, $1.5 \times 10^5$ or $1.5 \times 10^3$ pfu of wild-type PR8 or NS1-99 virus. Mice were then monitored during 3 weeks for survival. The results are given in Table 4. NS1-99 virus had an LD50 at least three logs higher than that of wild-type virus.

TABLE 4

Attenuation of NS1-99 virus in mice

| | Survivors Infecting dose (pfu): | | |
|---|---|---|---|
| Virus | $5 \times 10^6$ | $1.5 \times 10^5$ | $5 \times 10^3$ |
| WT PR8[1] | 1/5 | 1/5 | 1/5 |
| NS1-99 | 3/5 | 5/5 | 5/5 |

[1]Wild-type Influenza Virus A/PR/8/34.

7. EXAMPLE

Generation and Characterization of NS1 Truncation Mutants in Influenza B Virus

7.1 Materials and Methods

Experimental details are similar to those in Section 6.1. Two mutant influenza B viruses, B/610B5B/201 (B/201) and B/AWBY-234, 127-amino-acids and 90 amino acids in length (C-terminal truncated NS1 proteins), respectively (Norton et al., 1987 Virology 156:204; Tobita et al., 1990 Virology 174: 314) were derived from coinfection experiments in tissue culture involving B/Yamagata/1/73 (B/Yam) and A/Aichi/2/68 viruses in the presence of anti-A (H3N2) virus antibody. The growth of the mutant influenza viruses in embryonated eggs of various ages were compared to that of parental virus B/Yam, which possess a wild-type 281-amino-acid NS1 protein. Eggs of 6, 10 and 14 days of age were inoculated with approximately $10^3$ pfuof B/Yam, B/201 or B/AWBY-234 viruses, incubated at 35° C. for 2 days, and the viruses present in the allantoic fluid were titrated by an HA assay.

Further, the attenuation characteristics of B/201 and B/AWBY-234 viruses were determined in mice. Groups of three BALB/c mice were intranasally infected with $3 \times 10^5$ pfu of wild-type B/YAM or B/201 and B/AWBY-234 mutant viruses, and the ability of these viruses to replicate was determined by measuring viral titers in lungs at day 3 postinfection since wild-type B/Yam does not induce apparent signs of disease in mice.

7.2 Results

TABLE 5

Influenza B virus replication in embryonated chicken eggs.

| | Hemagglutination titer Age of eggs: | | |
|---|---|---|---|
| Virus | 6 days | 10 days | 14 days |
| B/Yam | 362 | 256 | <2 |
| B/201 | 32 | <2 | <2 |
| B/AWBY-234 | 8 | <2 | <2 |

The results from the growth of the mutant and wild-type influenza B viruses in embryonated chicken eggs, shown in Table 5, demonstrate that, as in the case with influenza A viruses, a carboxy-terminal truncation of the NS1 of influenza B virus is responsible for a lower replication yield in older embryonated chicken eggs which mount an efficient IFN response. This finding indicates that the NS1 of influenza B virus is also involved in inhibiting the IFN responses of the host, and that deletions on the NS1 gene of influenza B virus result in an attenuated phenotype.

The results from the replication experiments in mice are given in Table 6. B/201 and B/AWBY-234 virus titers were approximately three logs of magnitude lower that B/Yam titers, indicating that truncations of the carboxy-terminal domain of the NS1 of influenza B virus are responsible for an attenuated phenotype in mice.

TABLE 6

Influenza B virus replication in mouse lungs

| Virus | Lung titers at day 3 postinfection (pfu/lung) | | |
|---|---|---|---|
| B/Yam | $2 \times 10^4$ | $1 \times 10^4$ | $3 \times 10^4$ |
| B/201 | 30 | <10 | 60 |
| B/AWBY-234 | <10 | 40 | <10 |

8. PROTECTION AGAINST WILD-TYPE INFLUENZA VIRUS INFECTION IN MICE IMMUNIZED WITH INFLUENZA A AND B VIRUSES CONTAINING DELETIONS IN THEIR NS1 PROTEINS

In order to determine whether mice immunized with attenuated influenza A and B viruses containing truncated NS1 proteins were protected against challenge with their respective wild-type viruses the following experiment was carried out. BALB/c mice were immunized intranasally with A/NS1-99 virus and three weeks later they were infected with 100 $LD_{50}$ of wild-type influenza A/PR/8/34 virus. Immunized animals were protected against death, while all control naive mice died after the challenge (see Table 7). In a second experiment, BALB/c mice were intranasally immunized with the influenza B viruses B/201 or B/AWBY-234, expressing truncated NS1 proteins. Three weeks later the mice were challenged with $3 \times 10^5$ pfu wild-type influenza B/Yam/1/73 virus. Since this strain of influenza B virus does not induce disease symptoms in mice, the degree of protection was determined by measuring virus titers in lungs at day 3 post-challenge. While naive control animals had titers around $10^4$ pfu/lung, viruses were not detected in lungs of immunized animals (see Table 8). These findings suggest that influenza A as well as influenza B viruses containing modified NS1 genes are able to induce an immune response in mice which is fully protective against subsequent wild-type virus challenge.

TABLE 7

Survival of mice immunized with influenza A/NS1-99 virus after challenge with 100 $LD_{50}$ of wild-type influenza A/PR/8/34 virus.

| Immunizing Dose of A/NS1-99 Virus | Number of Survivors/Total |
|---|---|
| $5 \times 10^6$ pfu | 3/3 |
| $1.5 \times 10^5$ pfu | 4/4 |
| PBS | 0/5 |

TABLE 8

Lung titers in mice immunized with influenza B/201 and B/AWBY-234 viruses after challenge with $3 \times 10^5$ pfu of wild-type influenza B/Yamagata/73 virus.

| Immunizing Dose | Lung titers (pfu/lung) |
|---|---|
| $3 \times 10^5$ pfu of B/201 | $<10^1, <10^1, <10^1, <10^1, <10^1$ |
| $3 \times 10^5$ pfu of B/AWBY-234 | $<10^1, <10^1, <10^1, <10^1, <10^1$ |
| PBS | $2.5 \times 10^4, 1 \times 10^4, 1.7 \times 10^4, 3 \times 10^4, 5 \times 10^4$ |

9. EXAMPLE

Induction of Type I Interferon in Embryonated Eggs Infected with delNS1 Virus The ability of delNS1 virus, an influenza A virus lacking the NS1 gene, to induce type I IFN secretion in embryonated chicken eggs was next determined. For this purpose, groups of two 10-days-old embryonated chicken eggs were infected with $5 \times 10^3$ pfu of delNS1 or wild-type PR8 viruses. Eighteen hours postincubation at 37° C., the allantoic fluid was harvested and dialyzed against acid pH overnight, to inactivate infectious viruses. After acid pH treatment, samples were dialyzed against PBS, and they were tested for IFN activity by determining the highest dilution with protective activity against VSV infection (approximately 200 pfu) in CEF cells. The results shown in Table 9 indicate that in the absence of NS1, influenza A viruses are higher inducers of IFN.

TABLE 9

Induction of IFN in eggs.

| Virus | IFN (U/ml) |
|---|---|
| PR8 | <16, <16 |
| delNS1 | 400, 400 |
| mock | <16, <16 |

10. EXAMPLE

Antiviral Activity of delNS1 Virus

Elimination of the IFN antagonist (NS1) gene from influenza A virus may result in a virus with the ability to induce high levels of IFN. If this is the case, delNS1 virus will "interfere" with the replication of IFN-sensitive viruses. In order to test this possibility, Applicants investigated the ability of delNS1 virus to inhibit the replication of influenza A/WSN/33 (WSN) virus, a commonly used laboratory strain of influenza virus, in eggs. As can be seen in FIG. 1, treatment with only 2 pfu of delNS1 virus was able to reduce the final titers of WSN virus in the allantoic fluid by one log. In addition, treatment with $2 \times 10^4$ pfu of delNS1 virus resulted in practically complete abrogation of WSN replication in eggs. DelNS1 virus was also able to interfere with the replication in eggs of other influenza A virus strains (H1N1 and H3N2), influenza B virus and a different virus such as Sendai virus (FIG. 2).

Encouraged by these results, Applicants next determined the ability of delNS1 virus to interfere with wild-type influenza virus replication in mice. Although type I IFN treatment in tissue culture prevents influenza A virus replication in vitro, treatment of mice with IFN is not able to inhibit the replication of influenza viruses (Haller, 1981, Current Top Microbiol Immunol 92:25-52). This is true for most inbred strains of mice, except for A2G mice. A2G mice, as well as a significant proportion of wild mice (approximately 75%), contain at least one intact Mx1 allele, while most laboratory strains are Mx1-/- (Haller, 1986, Current Top Microbiol Immunol 127:331-337). The Mx1 protein, which is a homologue of the human MxA protein (Aebi, 1989, Mol. Cell. Biol. 11:5062), is a potent inhibitor of influenza virus replication (Haller, 1980, Nature 283:660). This protein is not constitutively expressed, but its expression is transcriptionally induced by type I IFN. Thus, A2G mice can be used to test the ability of IFN-inducers to stimulate an antiviral response against influenza A viruses (Haller, 1981, Current Top Microbiol Immunol 92:25-52).

Applicants intranasally infected eight 4-week-old A2G mice with $5 \times 10^6$ pfu of a highly pathogenic influenza A/PR/8/34 virus isolate (Haller, 1981, Current Top Microbiol Immunol 92:25-52). Half of the mice received an intranasal treatment with $5 \times 10^6$ pfu of delNS1 at −24 h with respect to the PR8 infection. The other four mice were treated with PBS. Body weight changes and survival was monitored. These results demonstrate that delNS1 treatment was able to protect A2G mice against influenza virus-induced death and body weight lost. The same treatment was not effective in Mx1−/− mice indicating that the mechanism of viral protection was Mx1, i.e. IFN, mediated.

11. EXAMPLE

Antitumor Properties of delNS1 Virus in Mice

Given that type I IFN and/or inducers of type I IFN have been shown to have antitumor activities (Belardelli and Gresser, 1996 Immunology Today 17: 369-372; Qin et al., 1998, Proc. Natl. Acad. Sci. 95: 14411-14416), it is possible that treatment of tumors with delNS1 virus might mediate tumor regression. Alternatively, delNS1 virus might have oncolytic properties, i.e., it may be able to specifically grow in and kill tumor cells, many of which are known to have deficiencies in the IFN system. In order to test anti-tumor activity of delNS1 virus, the following experiment was conducted using murine carcinoma cell line CT26 WT in a mouse tumor model for pulmonary metastasis (Restifo et al., 1998 Virology 249:89-97). $5 \times 10^5$ CT26 WT cells were injected intravenously into twelve 6-weeks-old BALB/c mice. Half of the mice were treated intranasally with $10^6$ pfu of delNS1 virus every 24 hours at days 1, 2 and 3 postinoculation. Twelve days after tumor injection, mice were sacrificed and lung metastases were enumerated. As shown in Table 10, delNS1 treatment mediated a significant regression of murine pulmonary metastases.

TABLE 10

Antitumor activity of delNS1 virus in BALB/C mice injected with CT26.WT tumor cells.

| | Number of pulmonary metastases | |
|---|---|---|
| | PBS-treated | delNS1-treated |
| Mouse 1 | >250 | 120 |
| Mouse 2 | >250 | 28 |
| Mouse 3 | >250 | 9 |
| Mouse 4 | >250 | 6 |
| Mouse 5 | >250 | 2 |
| Mouse 6 | >250 | 1 |

12. EXAMPLE

The NS1 Protein Inhibits the Translocation of IRF-3 During Influenza Virus Infection The results described herein suggest that the NS1 protein of influenza virus is responsible for the inhibition of the type I IFN response against the virus, and that mutations/deletions in this protein result in attenuated viruses due to an enhanced IFN response during infection. It is known that synthesis of type I IFN during viral infection can be triggered by double-stranded RNA (dsRNA). IRF-3 is a transcription factor which is usually found in an inactive form in the cytoplasm of mammalian cells. Double-stranded RNA induces the phosphorylation (activation) of the transcription factor IRF-3, resulting in its translocation to the nucleus, where it induces transcription of specific genes, including genes coding for type I IFN (Weaver et al., 1998, Mol. Cell. Biol. 18:1359). In order to determine if NS1 of influenza is acting on IRF-3, IRF-3 localization in CV1 cells infected with wild-type PR8 or with delNS1 influenza A virus was monitored. FIG. 3 shows that IRF-3 translocation is minimal in PR8-infected cells (in fewer than 10% of the cells). In contrast, approximately 90% of delNS1-infected cells showed nuclear localization of IRF-3. Strikingly, it was possible to partially inhibit the IRF-3 translocation in delNS1-infected cells by expressing NS1 from a plasmid in trans. The results demonstrate that the NS1 of influenza A virus is able to inhibit IRF-3 translocation in virus-infected cells. It is likely that the NS1 of influenza virus prevents dsRNA-mediated activation of IRF-3 by sequestering the dsRNA generated during viral infection, thus resulting in an inhibition of IFN synthesis.

The present invention is not to be limited in scope by the specific embodiments described which are intended as single illustrations of individual aspects of the invention, and any constructs or viruses which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference in their entireties.

What is claimed is:

1. A method for generating an attenuated influenza virus comprising:
   (a) introducing a recombinant DNA comprising the coding sequence of an influenza virus NS1 gene into a cell that provides the other influenza virus gene segments and viral proteins required to produce influenza virus particles, wherein the NS1 gene encodes a truncated NS1 protein composed of between 90 and 130 N-terminal amino acid residues of the NS1 protein of an influenza virus strain, so that the NS1 protein has an impaired ability to antagonize the cellular interferon response; and
   (b) culturing the cell, wherein the attenuated influenza virus is produced.

2. The method of claim 1, wherein the NS1 gene encodes a truncated NS1 protein of between 90 and 100 N-terminal amino acid residues of the NS1 protein of the influenza virus strain.

3. The method of claim 1, wherein the NS1 gene encodes a truncated NS1 protein of between 100 and 110 N-terminal amino acid residues of the NS1 protein of the influenza virus strain.

4. The method of claim 1, wherein the NS1 gene encodes a truncated NS1 protein of between 110 and 120 N-terminal amino acid residues of the NS1 protein of the influenza virus strain.

5. The method of claim 1, wherein the NS1 gene encodes a truncated NS1 protein of between 120 and 130 N-terminal amino acid residues of the NS1 protein of the influenza virus strain.

6. The method of claim 1, wherein one of the other influenza virus gene segments encodes a heterologous sequence.

7. The method of claim 6, wherein the heterologous sequence is an antigen of an influenza virus strain variant.

8. The method of claim 6, wherein the influenza virus gene segment encoding the heterologous sequence is the hemagglutinin or neuraminidase gene segment.

9. The method of claim 1, wherein the attenuated influenza virus is an influenza A virus.

10. The method of claim 1, wherein the attenuated influenza virus is an influenza B virus.

11. A method for generating an attenuated influenza virus comprising:
    (a) introducing a recombinant DNA comprising the coding sequence of an influenza virus NS1 gene into a cell that provides the other influenza virus gene segments and viral proteins required to produce influenza virus particles, wherein the NS1 gene encodes a truncated NS1 protein composed of between 60 and 70 N-terminal amino acid residues of the NS1 protein of an influenza virus strain, so that the NS1 protein has an impaired ability to antagonize the cellular interferon response; and
    (b) culturing the cell, wherein the attenuated influenza virus is produced.

12. The method of claim 11, wherein one of the other influenza virus gene segments encodes a heterologous sequence.

13. The method of claim 12, wherein the heterologous sequence is an antigen of an influenza virus strain variant.

14. The method of claim 12, wherein the influenza virus gene segment encoding the heterologous sequence is the hemagglutinin or neuraminidase gene segment.

15. The method of claim 11, wherein the attenuated influenza virus is an influenza A virus.

16. The method of claim 11, wherein the attenuated influenza virus is an influenza B virus.

17. A method for generating an attenuated influenza virus comprising:
(a) introducing a recombinant DNA comprising the coding sequence of an influenza virus NS1 gene into a cell that provides the other viral segments and viral proteins required to produce influenza virus particles, wherein the NS1 gene encodes a truncated NS1 protein composed of amino acid residues 1 to 130, amino acid residues 1 to 120, amino acid residues 1 to 110, amino acid residues 1 to 100, amino acid residues 1 to 99, amino acid residues 1 to 90, amino acid residues 1 to 89, amino acid residues 1 to 70, or amino acid residues 1 to 60 of the NS1 protein of an influenza virus strain, so that the NS1 protein has an impaired ability to antagonize the cellular interferon response; and
(b) culturing the cell, wherein the attenuated influenza virus is produced.

18. The method of claim 17, wherein one of the other influenza virus gene segments encodes a heterologous sequence.

19. The method of claim 18, wherein the heterologous sequence is an antigen of an influenza virus strain variant.

20. The method of claim 18, wherein the influenza virus gene segment encoding the heterologous sequence is the hemagglutinin or neuraminidase gene segment.

21. The method of claim 17, wherein the attenuated influenza virus is an influenza A virus.

22. The method of claim 17, wherein the attenuated influenza virus is an influenza B virus.

23. A method for generating an attenuated influenza virus comprising:
(a) introducing a recombinant DNA comprising the coding sequence of an influenza virus NS1 gene into a cell that provides the other influenza virus gene segments and viral proteins required to produce influenza virus particles, wherein the NS1 gene encodes a truncated NS1 protein composed of between 90 and 100, 100 and 110, or 70 and 80 N-terminal amino acid residues of the NS1 protein of an influenza virus strain, so that the NS1 protein has an impaired ability to antagonize the cellular interferon response, and wherein one of the other influenza virus gene segments encodes a heterologous sequence; and
(b) culturing the cell, wherein the attenuated influenza virus is produced.

24. The method of claim 23, wherein the influenza virus NS1 gene encodes a truncated NS1 protein composed of between 70 and 80 N-terminal amino acid residues of the NS1 protein of the influenza virus strain.

25. The method of claim 23, wherein the heterologous sequence is an antigen of an influenza virus strain variant.

26. The method of claim 23, wherein the influenza virus gene segment encoding the heterologous sequence is the hemagglutinin or neuraminidase gene segment.

27. The method of claim 23, wherein the attenuated influenza virus is an influenza A virus.

28. The method of claim 23, wherein the attenuated influenza virus is an influenza B virus.

* * * * *